United States Patent
Katchman et al.

(10) Patent No.: US 10,591,474 B2
(45) Date of Patent: Mar. 17, 2020

(54) POINT-OF-CARE FLUORESCENT IMMUNOASSAY FOR IDENTIFYING BIOMARKERS IN PATIENT BIOFLUID SAMPLES

(71) Applicant: Arizona Board of Regents on behalf of Arizona State University, Scottsdale, AZ (US)

(72) Inventors: Benjamin Katchman, Tempe, AZ (US); Karen Anderson, Scottsdale, AZ (US); Joseph Smith, Tempe, AZ (US); Jennifer Blain Christen, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/579,038

(22) PCT Filed: May 6, 2016

(86) PCT No.: PCT/US2016/031203
§ 371 (c)(1),
(2) Date: Dec. 1, 2017

(87) PCT Pub. No.: WO2016/195918
PCT Pub. Date: Dec. 8, 2016

(65) Prior Publication Data
US 2018/0172681 A1    Jun. 21, 2018

Related U.S. Application Data

(60) Provisional application No. 62/170,638, filed on Jun. 3, 2015.

(51) Int. Cl.
*G01N 33/543*  (2006.01)
*G01N 33/58*   (2006.01)
(Continued)

(52) U.S. Cl.
CPC .. *G01N 33/54373* (2013.01); *B01L 3/502715* (2013.01); *G01N 21/6428* (2013.01);
(Continued)

(58) Field of Classification Search
CPC ............ G01N 33/54373; G01N 33/58; G01N 33/6857; G01N 33/582; G01N 33/54386; G01N 21/6428; B01L 3/502715
See application file for complete search history.

(56) References Cited

U.S. PATENT DOCUMENTS 4,717,545 A * 1/1988 Morris ................. G01N 21/255
                                                    422/401
5,281,825 A * 1/1994 Berndt ................. G01N 21/255
                                                    250/458.1
(Continued)

FOREIGN PATENT DOCUMENTS

WO    2015168515 A1    11/2015
WO    2016195918 A1    12/2016

OTHER PUBLICATIONS

International Search Report and Written Opinion for International Patent Application No. PCT/US2016/031203 dated Sep. 15, 2016.
(Continued)

*Primary Examiner* — Melanie Brown
(74) *Attorney, Agent, or Firm* — Quarles & Brady LLP; Jessica L. Lewis

(57) ABSTRACT

Systems and methods for low-cost point-of-care immunoassay are provided. The system comprises an emitter, two optical interference filters, a microscope slide, a photodiode detector, a circuit, and a measuring unit. The detector is placed upon the second filter, the slide, the first filter, and then the emitter. The emitter comprises non-organic light emitting diodes (LEDs) or organic light emitting diodes (OLEDs) that emits light of a first color. The slide is spotted with biofluid from a patient. Biomarkers in the biofluid is
(Continued)

bound with immobilized fluorophores that emit light of a second color when stimulated by the light of the first color. The first and second filters band-pass the light of the first and second colors, respectively. The detector detects light of the second color. The current outputted from the detector is converted into a relatively-large output voltage by a circuit. A measuring unit measures the ramp time of the output voltage. The ramp time is to be used to determine the concentration of the fluorophores, which in turn is related to the concentration of the biomarkers.

14 Claims, 12 Drawing Sheets

(51) Int. Cl.
B01L 3/00 (2006.01)
G01N 21/64 (2006.01)
G01N 33/68 (2006.01)
(52) U.S. Cl.
CPC ....... *G01N 33/54386* (2013.01); *G01N 33/58* (2013.01); *G01N 33/582* (2013.01); *G01N 33/6857* (2013.01); *G01N 2333/025* (2013.01)

(56) References Cited

U.S. PATENT DOCUMENTS

| | | | | |
|---|---|---|---|---|
| 6,743,581 | B1* | 6/2004 | Vo-Dinh | C12Q 1/001 356/335 |
| 8,691,584 | B2* | 4/2014 | Durack | G01N 33/48 422/73 |
| 2003/0035755 | A1 | 2/2003 | Chen et al. | |
| 2003/0164295 | A1 | 9/2003 | Sterling | |
| 2003/0232427 | A1* | 12/2003 | Montagu | G01N 21/6428 435/287.2 |
| 2005/0157301 | A1 | 7/2005 | Chediak et al. | |
| 2005/0244953 | A1* | 11/2005 | Cohen | G01N 21/01 435/287.2 |
| 2008/0003664 | A1 | 1/2008 | Tysoe et al. | |
| 2008/0200342 | A1 | 8/2008 | Rao et al. | |
| 2008/0200344 | A1* | 8/2008 | Cheng | G01N 33/56983 506/9 |
| 2009/0261235 | A1 | 10/2009 | Lahav et al. | |
| 2009/0322677 | A1* | 12/2009 | Lee | G06F 3/0421 345/158 |
| 2010/0105035 | A1* | 4/2010 | Hashsham | G01N 21/645 435/6.19 |
| 2010/0122904 | A1* | 5/2010 | Hassibi | H01B 33/5438 204/403.01 |
| 2010/0136521 | A1 | 6/2010 | Yoon | |
| 2010/0141938 | A1 | 6/2010 | Banerjee et al. | |
| 2011/0235041 | A1* | 9/2011 | Rao | G08B 21/12 356/437 |
| 2012/0178632 | A1 | 7/2012 | McKeegan et al. | |
| 2013/0183676 | A1* | 7/2013 | Chen | G01N 21/6408 435/6.12 |
| 2017/0059563 | A1 | 3/2017 | Smith et al. | |

OTHER PUBLICATIONS

Anderson, K. et al., "Application of Protein Microarrays for Multiplexed Detection of Antibodies to Tumor Antigens in Breast Cancer", Journal of Proteome Research, Apr. 2008, vol. 7, No. 4, pp. 1490-1499 <DOI:10.1021/pr700804c>.
Anderson, K. et al., "Autoantibody Signature for the Serologic Detection of Ovarian Cancer", Journal of Proteome Research, 2015 (available online Nov. 2014), vol. 14, No. 1, pp. 578-586 <DOI:10.1021/pr500908n>.
Anderson, K. et al., "Biologic predictors of serologic responses to HPV in oropharyngeal cancer: The Hotspot study", Oral Oncology, Aug. 2015, vol. 51, No. 8, pp. 751-758 <DOI:10.1016/j.oraloncology.2015.05.007>.
Anderson, K. et al., "HPV16 antibodies as risk factors for oropharyngeal cancer and their association with tumor HPV and smoking status", Oral Oncology, Jul. 2015, vol. 51, No. 7, pp. 662-667 <DOI:10.1016/j.oraloncology.2015.04.011>.
Anderson, K. et al., "p53 autoantibodies as potential detection and prognostic biomarkers in serous ovarian cancer", Cancer Epidemiology, Biomarkers and Prevention, Mar. 2010, vol. 19, No. 3, pp. 859-868 <DOI:10.1158/1055-9965. EPI-09-0880>.
Anderson, K. et al., "Protein Microarray Signature of Autoantibody Biomarkers for the Early Detection of Breast Cancer", Journal of Proteome Research, Oct. 2010, vol. 10, No. 1, pp. 85-96 <DOI:10.1021/pr100686b>.
Anderson, K. et al., "Serum antibodies to the HPV16 proteome as biomarkers for head and neck cancer", British Journal of Cancer, Jun. 2011, vol. 104, No. 12, pp. 1896-1905 <DOI:10.1038/bjc.2011.171>.
Banerjee, A. et al., "Concentration dependence of fluorescence signal in a microfluidic fluorescence detector", Journal of Luminescence, Jun. 2010, vol. 130, No. 6, pp. 1095-1100 <DOI:10.1016/j.jlumin.2010.02.002>.
Broadhurst, M. et al., "ReEBOV Antigen Rapid Test kit for point-of-care and laboratory-based testing for Ebola virus disease: a field validation study", The Lancet, Aug. 2015 (available online Jun. 2015), vol. 386, No. 9996, pp. 867-874 <DOI:10.1016/S0140-6736(15)61042-X>.
Choi, J. et al., "Sensitive biomolecule detection in lateral flow assay with a portable temperature-humidity control device", Biosensors and Bioelectronics, May 2016, vol. 79, pp. 98-107 <DOI:10.1016/j.bios.2015.12.005>.
Combes, J. et al., "Antibodies against high-risk human papillomavirus proteins as markers for invasive cervical cancer", International Journal of Cancer, Nov. 2014, vol. 135, No. 10, pp. 2453-2461 <DOI:10.1002/ijc.28888>.
Cretich, M. et al., "Protein microarray technology: how far off is routine diagnostics?", The Analyst, Feb. 2014, vol. 139, No. 3, pp. 528-542 <DOI:10.1039/c3an01619f>.
Cuzick, J. et al., "Overview of human papillomavirus-based and other novel options for cervical cancer screening in developed and developing countries", Vaccine, Aug. 2008, vol. 26, Supplement 10, pp. K29-K41 <DOI:10.1016/j.vaccine.2008.06.019>.
Desmetz, C. et al., "Autoantibody signatures: progress and perspectives for early cancer detection", Journal of Cellular and Molecular Medicine, Oct. 2011, vol. 15, No. 10, pp. 2013-2024 <DOI:10.1111/i.1582-4934.2011.01355.x>.
Dixit, R. et al., "Simultaneous Single Detector Measurement of Multiple Fluorescent Sources", IEEE Sensors Journal, May 2013 (IEEE Date of Publication: Jan. 2013), vol. 13, No. 5, pp. 1965-1971 <DOI:10.1109/JSEN.2013.2239285>.
Dominguez, A. et al., "Development of a testbed for flexible a-Si:H photodiode sensing arrays", Proceedings of SPIE Defense, Security, and Sensing (Baltimore, MD, Apr. 29-May 3, 2013), May 2013, vol. 8730, article 87300H (8 pages) <DOI:10.1117/12.2015499>.
Dou, M. et al., "A versatile PDMS/paper hybrid microfluidic platform for sensitive infectious disease diagnosis", Analytical Chemistry, Jul. 2014, vol. 86, No. 15, pp. 7978-7986 <DOI:10.1021/ac5021694>.
D'Souza, G. et al., "Oral Human Papillomavirus (HPV) Infection in HPV-Positive Patients With Oropharyngeal Cancer and Their Partners", Journal of Clinical Oncology, Aug. 2014 (available online Apr. 2014), vol. 32, No. 23, pp. 2408-2415 <DOI:10.1200%2FJCO.2014.55.1341>.
D'Souza, G. et al., "The role of HPV in head and neck cancer and review of the HPV vaccine", Preventive Medicine, Oct. 2011, vol. 53, Supplement 1, pp. S5-S11 <DOI:10.1016/j.ypmed.2011.08.001>.
Forrest, S. et al., "Measuring the Efficiency of Organic Light Emitting Devices", Advanced Materials, Jul. 2003, vol. 15, No. 13, pp. 1043-1048 <DOI:10.1002/adma.200302151>.
Goodman, A., "HPV testing as a screen for cervical cancer", British Medical Journal, Jun. 2015, vol. 350, h2372 (14 pages) <DOI:10.1136/bmj.h2372>.

(56) References Cited

OTHER PUBLICATIONS

Hu, J. et al., "Advances in paper-based point-of-care diagnostics", Biosensors and Bioelectronics, Apr. 2014, vol. 54, pp. 585-597 <DOI:10.1016/j.bios.2013.10.075>.
Hu, J. et al., "Oligonucleotide-linked gold nanoparticle aggregates for enhanced sensitivity in lateral flow assays", Lab on a Chip, Nov. 2013, vol. 13, No. 22, pp. 4352-4357 <DOI:10.1039/c3lc50672j>.
Katchman, B. et al., "Application of flat panel OLED display technology for the point-of-care detection of circulating cancer biomarkers", Scientific Reports, Jul. 2016, vol. 6, article 29057 (11 pages).
Kreimer, A. et al., "Evaluation of human papillomavirus antibodies and risk of subsequent head and neck cancer", Journal of Clinical Oncology, Jul. 2013, vol. 31, No. 21, pp. 2708-2715 <DOI:10.1200/JCO.2012.47.2738>.
Lee, L. et al., "A Low-Cost, High-Performance System for Fluorescence Lateral Flow Assays", Biosensors, Dec. 2013, vol. 3, pp. 360-373 <DOI:10.3390/bios3040360>.
Marrs, M. et al., "Flexible amorphous silicon PIN diode x-ray detectors", Proceedings of SPIE Defense, Security, and Sensing (Baltimore, MD, Apr. 29-May 3, 2013), May 2013, vol. 8730, article 87300C (7 pages) <DOI:10.1117/12.2015917>.
Moody, C. et al., "Human papillomavirus oncoproteins: pathways to transformation", Nature Reviews. Cancer, Aug. 2010, vol. 10, No. 8, pp. 550-560 <DOI:10.1038/nrc2886>.
Nichols, J., "Reducing medical errors at the point of care", Laboratory Medicine, May 2005, vol. 36, No. 5, pp. 275-277 <DOI:10.1309/NXXWJ31PWFHT7L1Q>.
O'Brien, B. et al., "'14.7' Active Matrix PHOLED Displays on Temporary Bonded PEN Substrates with Low Temperature IGZO TFTs", Society for Information Display International Symposium Digest of Technical Papers, 2013, vol. 70-2L, pp. 447-450 <DOI:10.1002/j.2168-0159.2013.tb06243.x>.
O'Farrell, B., "Lateral Flow Technology for Field-Based Applications—Basics and Advanced Developments", Topics in Companion Animal Medicine, Dec. 2015, vol. 30, No. 4, pp. 139-147 <DOI:10.1053/j.tcam.2015.12.003>.
O'Farrell, B., Lateral Flow Immunoassay Systems: Evolution from the Current State of the Art to the Next Generation of Highly Sensitive, Quantitative Rapid Assays, in: Wild, D., "The Immunoassay Handbook" (Elsevier, 2013, available online Feb. 2013), pp. 89-107.
Pais, A. et al., "High-sensitivity, disposable lab-on-a-chip with thin-film organic electronics for fluorescence detection", Lab on a Chip, May 2008 (available online Mar. 2008), vol. 8, No. 5, pp. 794-800 <DOI:10.1039/B715143H>.
Parolo, C. et al., "Enhanced lateral flow immunoassay using gold nanoparticles loaded with enzymes", Biosensors and Bioelectronics, Feb. 2013, vol. 40, No. 1, pp. 412-416 <DOI:10.1016/j.bios.2012.06.049>.
Patent Cooperation Treaty, International Searching Authority, International Preliminary Report on Patentability for PCT/US2015/028734, 9 pages, report dated Nov. 1, 2016, opinion dated Jul. 28, 2015.
Patent Cooperation Treaty, International Searching Authority, International Preliminary Report on atentability for PCT/US2016/031203, 8 pages, report dated Dec. 5, 2017, opinion dated Sep. 15, 2016.
Patent Cooperation Treaty, International Searching Authority, International Search Report for PCT/US2015/028734, 3 pages, dated Jul. 28, 2015.
Patent Cooperation Treaty, International Searching Authority, International Search Report for PCT/US2016/031203, 4 pages, dated Sep. 15, 2016.
Pedersen, J. et al., "Early detection of cancer in the general population: a blinded case-control study of p53 autoantibodies in colorectal cancer", British Journal of Cancer, Jan. 2013, vol. 108, No. 1, pp. 107-114 <DOI:10.1038/bjc.2012.517>.
Perkins, M. et al., "What Ebola tells us about outbreak diagnostic readiness", Nature Biotechnology, May 2015, vol. 33, No. 5, pp. 464-469 <DOI:10.1038/nbt.3215>.
Petryayeva, E. et al., "Toward point-of-care diagnostics with consumer electronic devices: the expanding role of nanoparticles", RSC Advances, 2015, vol. 5, pp. 22256-22282 <DOI:10.1039/c4ra15036h>.
Porter, M., "What is value in health care?", New England Journal of Medicine, Dec. 2010, vol. 363, No. 26, pp. 2477-2481 <DOI:10.1056/NEJMp1011024>.
Qin, C. et al., "The Assessment of the Readiness of Molecular Biomarker-Based Mobile Health Technologies for Healthcare Applications", Scientific Reports, Dec. 2015, vol. 5, article 17854 (14 pages) <DOI:10.1038/srep17854>.
Quesada-González, D. et al., "Nanoparticle-based lateral flow biosensors", Biosensors and Bioelectronics, Nov. 2015, vol. 73, pp. 47-63 <DOI:10.1016/j.bios.2015.05.050>.
Ramachandran, N. et al., "Next-generation high-density self-assembling functional protein arrays", Nature Methods, May 2008, vol. 5, pp. 535-538 <DOI:10.1038/NMETH.1210>.
Ramachandran, N. et al., "Tracking humoral responses using self assembling protein microarrays," Proteomics Clinical Applications, Oct. 2008, vol. 2, pp. 1518-1527 <DOI:10.1002/prca.200800034>.
Rattle, S., "Lab-on-a-Chip, Micro- and Nanoscale Immunoassay Systems, and Microarrays", in: Wild, D., "The Immunoassay Handbook" (Elsevier, 2013, available online Feb. 2013), pp. 175-202.
Raupp, G. et al., "Low Temperature Amorphous Silicon Backplane technology development for Flexible displays in a Manufacturing Pilot line environment", Journal of the Society for Information Display, 2007, vol. 15, pp. 445-454 <DOI:10.1889/1.1828693>.
Reed, G. et al., "Use of coefficient of variation in assessing variability of quantitative assays", Clinical and Diagnostic Laboratory Immunology, Nov. 2002, vol. 9, No. 6, pp. 1235-1239 <DOI:10.1128/CDLI.9.6.1235-1239.2002>.
Reuschenbach, M. et al., "Characterization of humoral immune responses against p16, p53, HPV16 E6 and HPV16 E7 in patients with HPV-associated cancers", International Journal of Cancer, Dec. 2008, vol. 123, No. 11, pp. 2626-2631 <DOI:10.1002/ijc.23837>.
Rusling, J. et al., "Measurement of biomarker proteins for point-of-care early detection and monitoring of cancer", The Analyst, May 2010, vol. 135, No. 10, pp. 2496-2511 <DOI:10.1039/C0AN00204F>.
Ryu, G. et al., "Highly sensitive fluorescence detection system for microfluidic lab-on-a-chip", Lab on a Chip, May 2011 (available online Mar. 2011), vol. 11, No. 9, pp. 1664-1670 <DOI:10.1039/C0LC00586J>.
Seiler, C. et al., "DNASU plasmid and PSI:Biology-Materials repositories: resources to accelerate biological research", Nucleic Acids Research, Jan. 2014, vol. 42, No. D1, pp. D1253-D1260 <DOI:10.1093/nar/gkt1060>.
Sharma, S. et al., "Point-of-Care Diagnostics in Low Resource Settings: Present Status and Future Role of Microfluidics", Biosensors, Aug. 2015, vol. 5, No. 3, pp. 577-601 <DOI:10.3390/bios5030577>.
Smith, E. et al., "Risk factors and survival by HPV-16 E6 and E7 antibody status in human papillomavirus positive head and neck cancer", International Journal of Cancer, Jul. 2010, vol. 127, No. 1, pp. 111-117 <DOI:10.1002/ijc.25015>.
Smith, J. et al., "Application of Flexible OLED Display Technology for Electro-Optical Stimulation and/or Silencing of Neural Activity", Journal of Display Technology, Jun. 2014 (Date of Publication: Feb. 2014), vol. 10, No. 6, pp. 514-520 <DOI:10.1109/JDT.2014.2308436>.
Smith, J. et al., "Application of Flexible OLED Display Technology to Point-of-Care Medical Diagnostic Testing", Journal of Display Technology, Mar. 2016 (Date of Publication: Sep. 2015), vol. 12, No. 3, pp. 273-280 <DOI:10.1109/JDT.2015.2479457>.
Smith, J. et al., "Disposable Point-of-Use Optical Biosensor for Multiple Biomarker Detection", IEEE Biomedical Circuits and Systems Conference Proceedings (Lausanne, Switzerland, Oct. 22-24, 2014), (Date Added to IEEE Xplore: Dec. 2014), pp. 268-271 <DOI:10.1109/BioCAS.2014.6981714>.

(56) References Cited

OTHER PUBLICATIONS

Smith, J. et al., "Flexible Digital x-ray technology for far-forward remote diagnostic and conformal x-ray imaging applications", Proceedings of SPIE Defense, Security, and Sensing (Baltimore, MD, Apr. 29-May 3, 2013), May 2013, vol. 8730, article 87300F (7 pages) <DOI:10.1117/12.2016102>.

Smith, J. et al., "Flexible ISFET Biosensor Using IGZO Metal Oxide TFTs and an ITO Sensing Layer", IEEE Sensors Journal, Apr. 2014 (IEEE Date of Publication: Dec. 2013), vol. 14, No. 4, pp. 937-938 <DOI:10.1109/JSEN.2013.2295057>.

Song, C. et al., "Rapid and sensitive detection of β-agonists using a portable fluorescence biosensor based on fluorescent nanosilica and a lateral flow test strip", Biosensors and Bioelectronics, Dec. 2013, vol. 50, pp. 62-65 <DOI:10.1016/j.bios.2013.06.022>.

St John, A. et al., "Economic Evidence and Point-of-Care Testing", The Clinical Biochemist Reviews, Aug. 2013, vol. 34, No. 2, pp. 61-74.

TDR Diagnostics Evaluation Expert Panel. et al., "Evaluation of diagnostic tests for infectious diseases: general principles", Nature Reviews. Microbiology, Dec. 2010, vol. 8, Supplement 12, pp. S17-S29.

Tighe, P. et al., "ELISA in the multiplex era: potentials and pitfalls", Proteomics Clinical Applications, Apr. 2015, vol. 9, No. 3-4, pp. 406-422 <DOI:10.1002/prca.201400130>.

Vashist, S. et al., "Emerging Technologies for Next-Generation Point-of-Care Testing", Trends in Biotechnology, Nov. 2015, vol. 33, No. 11, pp. 692-705 <DOI:10.1016/j.tibtech.2015.09.001>.

Wagner, S. et al., "Materials for stretchable electronics", MRS Bulletin, Mar. 2012, vol. 37, No. 3, pp. 207-213 <DOI:10.1557/mrs.2012.37>.

Wang, J., "Electrochemical biosensors: Towards point-of-care cancer diagnostics", Biosensors and Bioelectronics, Apr. 2006, vol. 21, No. 10, pp. 1887-1892 <DOI:10.1016/j.bios.2005.10.027>.

Wilkinson, C. et al., "Enhanced performance of pulse driven small area polyfluorene light emitting diodes", Applied Physics Letters, Jul. 2001, vol. 79, pp. 171-173 <DOI:10.1063/1.1383799>.

Woodman, C. et al., "The natural history of cervical HPV infection: unresolved issues", Nature Reviews—Cancer, Jan. 2007, vol. 7, No. 1, pp. 11-22 <DOI:10.1038/nrc2050>.

Wu, G. et al., "Low-cost tools for diagnosing and monitoring HIV infection in low-resource settings", Bull World Health Organization, Dec. 2012, vol. 90, No. 12, pp. 914-920 <DOI:10.2471/BLT.12.102780>.

Xu, Y. et al., "Fluorescent Probe-Based Lateral Flow Assay for Multiplex Nucleic Acid Detection", Analytical Chemistry, Jun. 2014, vol. 86, No. 12, pp. 5611-5614 <DOI:10.1021/ac5010458>.

Yetisen, A. et al., "Paper-based microfluidic point-of-care diagnostic devices", Lab on a Chip, May 2013, vol. 13, No. 12, pp. 2210-2251 <DOI:10.1039/C3LC50169H>.

\* cited by examiner

FIGS. 8A-8C
A) HPV16 E7 IgG Positive
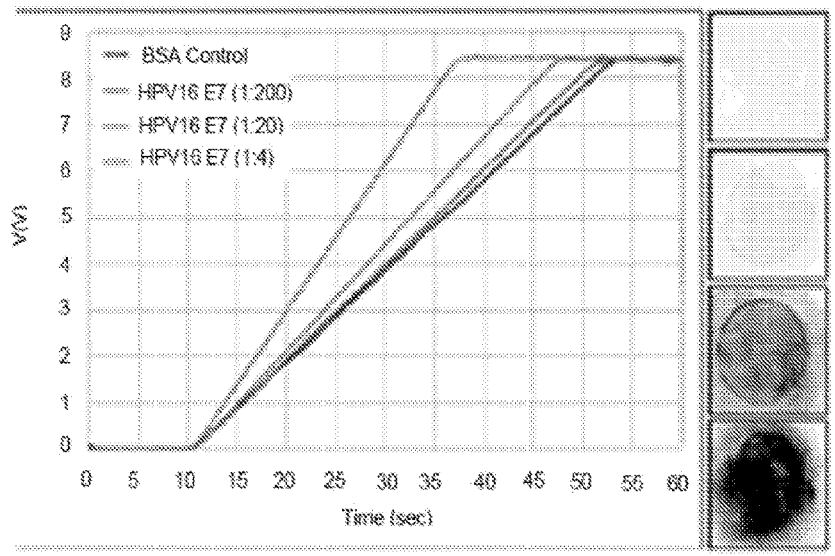
HPV16 E7 IgG Negative
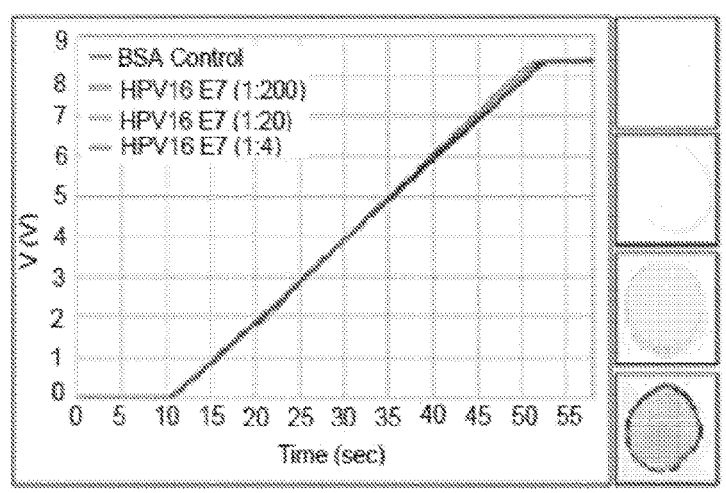

FIGS. 8A-8C, CONTINUED (B)

Intra Assay Variability

| Day | HPV16 E7 IgG Positive | | Human IgG | |
|---|---|---|---|---|
| | Mean | SEM | Mean | SEM |
| 1 | 18.74 | 1.74 | 5.08 | 0.12 |
| 2 | 17.98 | 0.34 | 4.77 | 0.27 |
| 3 | 14.54 | 1.18 | 4.99 | 0.31 |
| 4 | 14.44 | 1.00 | 3.08 | 0.52 |

(C)

Inter Assay Variability

| HPV16 E7 IgG Positive | | | Human IgG | | |
|---|---|---|---|---|---|
| Mean | St. Dev. | % CV | Mean | St. Dev. | % CV |
| 16.43 | 2.26 | 13.73 | 4.48 | 0.94 | 21.03 |

POINT-OF-CARE FLUORESCENT IMMUNOASSAY FOR IDENTIFYING BIOMARKERS IN PATIENT BIOFLUID SAMPLES

CROSS-REFERENCE TO RELATED APPLICATIONS

This application represents the national stage entry of PCT International Application No. PCT/US2016/031203 filed on May 6, 2016, and claims priority to U.S. Provisional Patent Application No. 62/170,638, filed Jun. 3, 2015. The disclosure of each of the above-identified applications is incorporated herein by reference as if set forth in its entirety.

STATEMENT REGARDING FEDERALLY SPONSORED RESEARCH

This invention was made with government support under 1521904 awarded by the National Science Foundation. The government has certain rights in the invention.

BACKGROUND

Centralized clinical testing of diagnostics is expensive and time consuming, causing delays in health care delivery. Recently, there have been substantial efforts in both the development and the availability of rapid point-of-care diagnostic assays for use in both clinical and non-clinical settings that address a variety of diseases and medical conditions. This has led the Food and Drug Administration, as well as the World Health Organization, to set forth suggested requirements and define a simple point-of-care device as fulfilling the ASSURED criteria (affordable, sensitive (>43%), specific (98%), user-friendly, reproducible/rapid, equipment free, and deliverable to those in need with no operator analysis or intervention).

Human papillomavirus (HPV) infection is the most commonly-diagnosed sexually-transmitted disease in the United States. Persistent infection with high-risk HPV has been demonstrated to play a role in several cancers. Most significantly, it has been demonstrated that high-risk HPV causes most, if not all, cervical cancers (99.7%) as well as oropharyngeal head and neck squamous cell carcinoma (45-90%). In the case of cervical cancer, screening for precursors by cytology (Papanicolaou test) has been successful in countries with adequate resources. However, guidelines in the United States and Europe recommend HPV testing in addition to cytology in women over the age of 30 (WHO and CDC). Currently, testing for HPV consists of a DNA screen at a clinical diagnostic laboratory.

Thus, there is a need for a rapid, low-cost, highly sensitive and specific diagnostic assay for the detection of HPV that can be performed in a non-clinical setting. A prior method can be used to identify antibodies for the HPV16 E7 in invasive cervical cancer and head and neck cancer screenings. However, this assay requires a complicated biochemistry sequence that is not feasible in a low-cost point-of-care device.

Also, current point-of-care diagnostic assays lack the ability to provide quantitative diagnostic information. This limits the ability of clinicians to accurately diagnose patients and accurately monitor their disease progression or response to a particular therapy.

Therefore, low-cost point-of-care immunoassay systems and methods that provide quantitative diagnostic information are needed.

SUMMARY

The present disclosure overcomes the aforementioned drawbacks by providing low-cost point-of-care immunoassay systems and methods that provide quantitative diagnostic information. Biofluid and fluoropores are bound with each other and spotted onto a microscope slide. When shone with light from non-organic light emitting diodes (LEDs) or organic light emitting diodes (OLED), the fluoropores emit light of a different color. The systems and methods use inexpensive optical interference filters to reduce the cost of optics. The filters are sandwiched with a microscope slide to increase the sensitivity of the assay. The current generated from photodiodes in response to the light from fluorophores are converted into relatively-large voltage output. The ramp time of the voltage output is inversely proportional to the concentration of fluorophores in the biofluid. The concentration of fluorophores is related to the concentration of biomarkers. Thus, quantitative measurements of biomarkers can be provided.

In accordance with one aspect of the disclosure, a system for low-cost point-of-care immunoassay is provided. The system comprises an emitter, two optical interference filters, a microscope slide, a photodiode detector, a circuit, and a measuring unit. The detector is placed upon the second filter, the slide, the first filter, and then the emitter. The emitter comprises organic light emitting diodes that emits light of a first color when pulsed with electrical current. The slide is spotted with biofluid from a patient. Biomarkers in the biofluid is bound with immobilized fluoropores that emit light of a second color when stimulated by the light of the first color. The first and second filters band-pass the light of the first and second colors, respectively. The detector detects light of the second color. The current outputted from the detector is converted into a relatively-large output voltage by a circuit. A measuring unit measures the ramp time of the output voltage. The ramp time is to be used to determine the concentration of the fluorophores.

In accordance with another aspect of the disclosure, a method for providing quantitative diagnostic information is provided. The steps of the method comprise preparing a microscope slide spotted with biofluid from a patient, assembling a layered structure with the slide, detecting light from the layered structure, converting current generated by the light into a relatively-large voltage output, measuring the ramp time of the voltage output, determining the concentration of fluorophores in the biofluid using the ramp time, and lastly generating a report using the concentration. On the microscope slide, fluorophores are immobilized and bound with the biomarkers. The layered structure is assembled as a non-organic light emitting diode or an organic light emitting diode emitter over a first optical interference filter, the slide, a second optical interference filter, and a photodiode detector. The emitter emits light of a first color and the fluorophores emit light of a second color when stimulated by the light of the first color. The first filter band-passes the light of the first color and the second filter band-passes the light of the second color. The detector outputs current when it detects light.

In accordance with yet another aspect of the disclosure, a method of immunoassay to be used for identifying biomarkers in a sample of patient biofluid is provided. The method comprises silanizing a microscope slide, spotting captured proteins onto the slide, incubating the proteins with the patient biofluid; and incubating the proteins further with detection antibodies associated with the biomarkers.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

FIGS. 8A-8C demonstrate detection of HPV antibodies in human sera. (a) Recombinant HPV16 E7 protein was immobilized and specifically detected serum HPV16 E7 antibodies over a series of dilutions. Representative images and ramp plots demonstrate assay specificity and background or off-target signal levels. To determine intra and inter assay variability we screened serum positive for HPV16 E7 antibodies and control serum in duplicate over four consecutive days. (b) Calculation of intra assay standard error of the mean and (c) inter assay coefficient of variance.

DETAILED DESCRIPTION

Systems and methods for low-cost point-of-care immunoassay that provide quantitative diagnostic information are provided. A much simpler biochemical procedure is used and suitable for a point-of-care setting with comparable clinical accuracy. The systems and methods also offer a wide dynamic range and a clinical-level sensitivity. Identifying the HPV16 E7 antibody biomarker in human sera is provided as an example herein. A person skilled in the art would appreciate that the systems and methods as disclosed herein can be applied to other biofluid—such as blood, saliva, sweat and urine—and other biomarkers of antibody or proteins for targeting antigens (e.g., HIV, Hepatitis B, Dengue, Ebola, and Cancer antigens).

Figure 1:
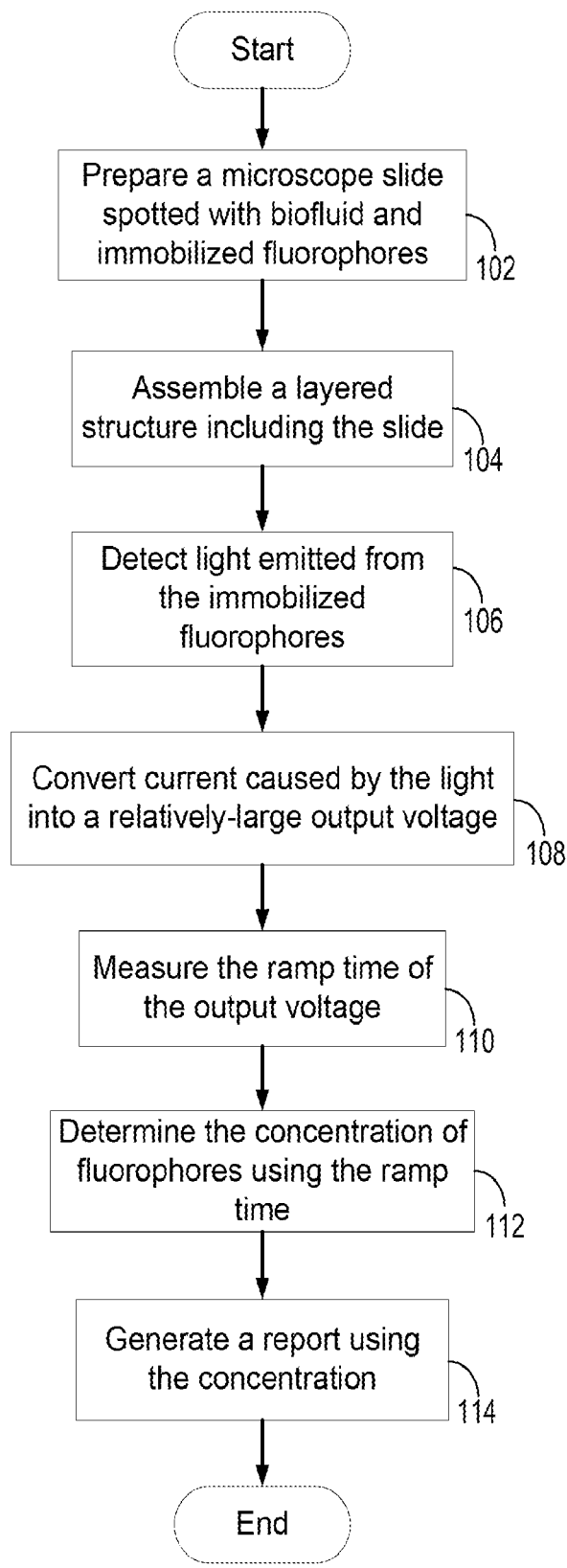
FIG. 1 is a flowchart illustrating an example method implemented according to the present application.

Referring to FIG. 1, a flowchart illustrating an example method implemented according to the present application is provided. First, in step 102, a microscope slide is prepared. The slide is spotted with the biomarker of interest, patient biofluid is then incubated on the slide with the biomarker of interest. The biomarker in the patient biofluid is then incubated with the detection reagent conjugated to the fluorophores. In the serological assay, patient's antibodies are incubated on the slide surface. The immobilized fluorophores are bound to the Fc portion of the patient's antibodies. Unbound immobilized fluorophores are washed away. The fluorophores that are bound to biomarkers in the biofluid, when stimulated by light, emit light of a different color.

Figure 2:
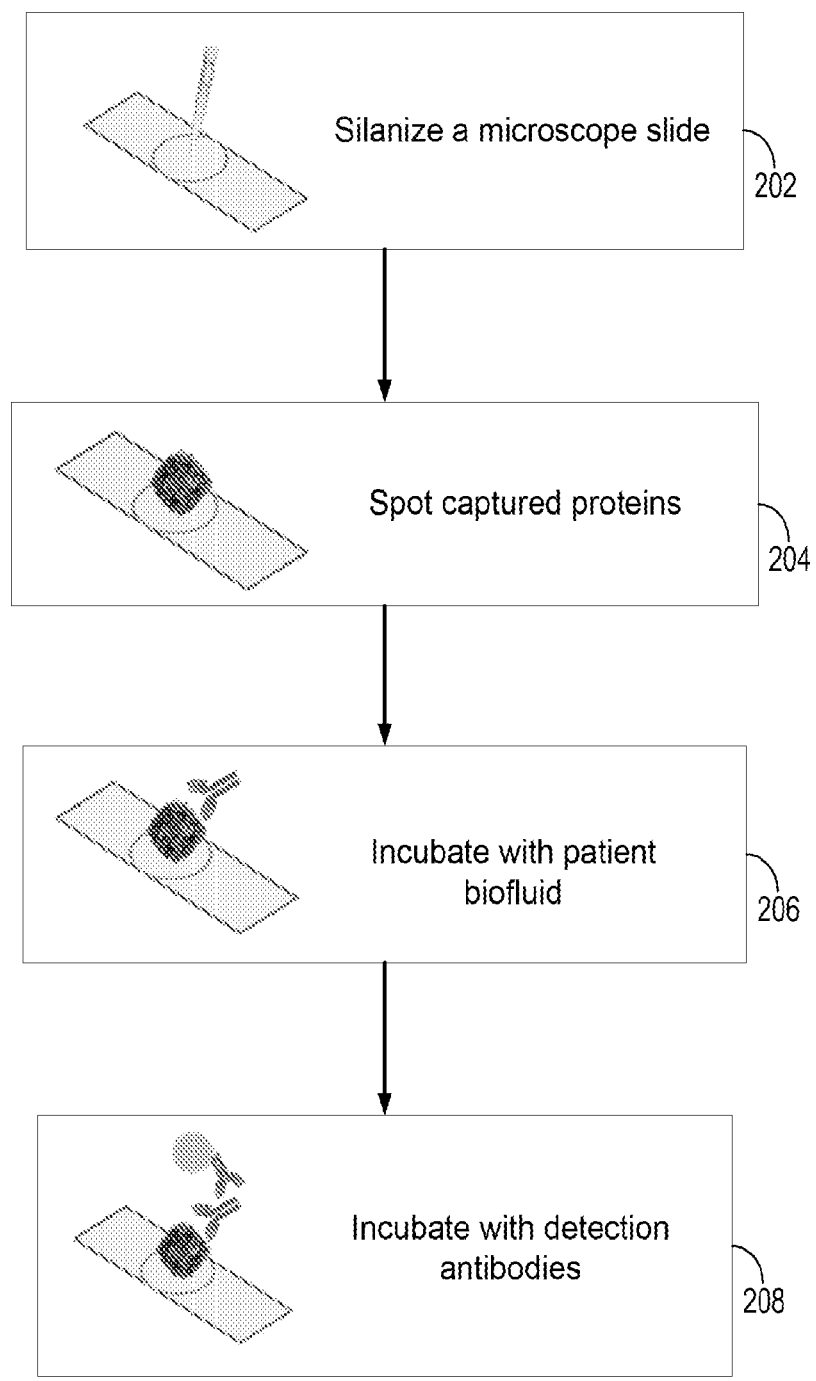
FIG. 2 is a flowchart illustrating an example method of preparing a microscope slide.

Referring to FIG. 2, a flowchart illustrating an example procedure of preparing a microscope slide to be used for diagnosis later is provided. In step 202, a glass microscope slide is silanized. For example, the slide is coated with a 2% aminosilane coating solution for 15 minutes at room temperature, rinsed with acetone followed by distilled water, and then dried with filtered compressed air. The slide is stored at room temperature until it is used. In step 204, captured proteins are spotted onto the slide. For example, purified recombinant HPV16 E7 protein is diluted in distilled water to 25 μg/mL and spotted (5 μl) on the aminosilanated glass slide and allowed to dry at room temperature. The protein (HPV16 E7 and BSA) spotting procedure can be repeated multiple times. Detected signal strength and thus the detection sensitivity increase as the number of times of repeating spotting procedure increases. The slide is stored at 4° C. overnight.

In step 206 of the example procedure for preparing a microscope slide, the slide is incubated with patient biofluid. For example, in the following morning, the slide is washed once in phosphate buffered saline pH 7.4-0.2% Tween20 ("PBST") solution and blocked at room temperature in 5% milk-PBST for one hour. During blocking, the serum samples are diluted 1:1 in a 5% milk-PBST and allowed to incubate at room temperature. The slide is then removed from the blocking solution and incubated with the serum for 1 hour at room temperature. The slide is then rinsed once in PBST. Lastly, in step 208, the slide is incubated with detection antibodies. In one configuration, the presence of human IgG antibodies to HPV16 E7 is detected by Dylight 549-conjugated AffiniPure Goat Anti-Human IgG. A positive control can be obtained by probing the purified HPV16 E7 recombinant protein with a mouse monoclonal antibody to HPV16 E7 and detected it with anti-mouse IgG AlexaFluor 555. The cut-off values for serum positive for HPV16 E7 can be defined as 3 standard deviations+the mean of the control (HPV16 E7—and healthy controls). This preparation procedure requires fewer steps than a prior method of ELISA-type assays and allows the assay as disclosed herein to be translated into a rapid low-cost point-of-care immunoassay without compromising sensitivity.

In one configuration, targeted antibody—HPV Antibody—is captured and prepared with the following procedures.

First, the presence of the HPV16 E7 IgG antibodies is tested in serum samples (1:100) by programmable RAPID ELISA. Proteins are expressed using a human HeLa cell lysate in vitro transcription and translation system and blocked with 10% *Escherchia coli* (*E. coli*) lysate. Luminescence is measured as Relative Light Units (RLU) as a ratio to GST-antigen control. Cut-off values for positive serology are defined as the mean+3 standard deviations of the RLU ratio observed among healthy controls.

Then, the antibody is expressed and purified. Full length HPV16 E7 gene is transferred into gateway compatible destination PCPD nHalo vector from pDONR221 vector by recombination cloning. Expression plasmids are transformed into *E. coli* strain BL21DE3 and isolated colonies are grown in LB media for 6-8 hours at 37° C. The cultures are then diluted into MJ9 media and grown at 37° C. until OD600 of 0.6 is reached and induced with IPTG at 18° C. for 21 hours. After a 21-hour incubation at 18° C., the cells are centrifuged at 5000×g for 20 minutes at 4° C., resuspended pellets in lysis buffer (50 mM HEPES, 150 mM NaCl, pH 7.5, IGEPAL 0.01%, 1 mM DTT, 25 µg/ml DNase, 2 mg/ml Lysozyme, 5 mM MgSO4, 100 µM PMSF). The culture is frozen to −20° C., thawed to RT and mixed for 1 hour at 37° C. The lysate is centrifuged at 5000×g for 20 minutes at 4° C. and the supernatant is removed and mixed with Halo Tag beads and allowed to bind O/N at 4° C. The beads are washed three times with purification buffer. E7 protein is eluted from halo tag beads by TEV protease. Bradford assay is used to quantitate the protein. Purity of E7 is determined by sodium dodecyl sulfate (SDS) poly acrylamide gel electrophoresis (PAGE).

To maximize rapid immunoassay sensitivity and specificity, fluorescent-based biorecognition is used in the systems and methods as disclosed herein. In fluorescent-based biorecognition, after a biorecognition site is spotted on a microscope slide in step 102, the slide is then actively interrogated by a bright light source and the weak emitted signals from the fluorescently-labeled immobilized fluorophores are detected electronically. Unfortunately, the fluorescence-based measurement equipment used in a typical clinical diagnostic laboratory requires large and expensive optical components that would be too expensive and inconvenient for point-of-care applications. In a prior attempted configuration for simple and low-cost alternative fluorescence-based measurement, magnifying optics is not required and the biorecognition detection layer is sandwiched between an non-organic light emitting diode (LED) or organic light emitting diode (OLED) emitter and a solid-state photodetector. The LED or OLED emitter replaces the laser light source, while the photodetector replaces the low-light digital camera used in typical clinical laboratories for fluorescence-based measurement. However, poor light attenuation through the orthogonally-crossed polarizers in the prior sandwich-style optics configurations significantly limit sensitivity, rendering these devices ineffective in providing clinical-level diagnostic sensitivity.

The devices and methods as disclosed herein replace the crossed polarizers with optical interference filters, and combine with charge integration technique for signal readout, which yield a clinical-level diagnostic sensitivity. Thus, much of the fluorescent measurement instrument functionality found in a typical diagnostic laboratory is miniaturized into a small and inexpensive configuration as disclosed herein.

Referring again to FIG. 1, after a microscope slide is prepared in step 102, a layered structure centered around the slide is assembled in step 104. An example layered structure as disclosed herein is provided in FIG. 3. The microscope slide 306 is sandwiched between an OLED emitter 310 and a photodiode detector 302 of a size similar to the emitter 310. For example, a microscope slide 306 is sandwiched between a 5 mm$^2$ green OLED emitter 310 and a similarly sized 2 mm×2 mm silicon photodiode light detector 302. Note the OLED emitter 310 is covered by an optical interference filter 308 and the detector 302 covers another optical interference filter 304. Example filters can be Chroma® optical filters. The two filters 304 and 308 bandpass different spectrums of the light and block light outside of those spectrums. For example, the emitter 310 can be a green OLED emitter, the fluorophores are green excite/orange emit ones, and filter 308 band-passes green light and filter 304 band-passes orange light. Light of colors other than green or orange is blocked by filter 308 or 304, respectively. A 3D printed assembly is designed and fabricated to align the microscope slide with the centers of the filters. In one configuration, a green OLED emitter is used. It has a peak emission intensity at 515 nm. In operation, the green OLED is pulsed at 6 Hz with an 8.8 volt forward bias, which provides an instantaneous optical output power of 0.8 mW. The green OLED emitter is then mounted in the base of a printed 3D assembly with a 520 nm/40 nm bandpass Chroma optical excitation filter positioned on top, and a 605 nm/70 nm long pass Chroma optical emission filter mounted in a groove above the slot used for inserting the microscope slides. Instead of Chroma optical interference filters, a high-volume (>100,000 units), much cheaper, comparable optical filter set can also be used. In another configuration, when the OLED emitter is being produced in a production configuration, thin film dielectric layers can be deposited on the starting OLED display substrate to be used as the green OLED excitation optical filter.

In operation, the OLED in the layered structure is activated to illuminate the immobilized fluorescent biorecognition site on the microscope slide. Any illuminated fluorescent material captured on the biorecognition site re-emits light of a different wavelength. For example, if green excite/orange emit fluorophores are used, longer wavelength orange light is emitted after the slide is shone with green light for an OLED emitter. The emitted orange light from the fluorophores then passes through the long pass optical filter 304, and then is detected by the photodiode 302, while the shorter wavelength light from the green OLED 310 is blocked by the same long pass optical filter 304. This sandwich-style optics configuration prevents the weak fluorescence light emitted by the fluorophores from being swamped out by the bright light from the OLED emitter, and enables point-of-care diagnostic sensitivity at a level that approaches a clinical laboratory.

Figure 3:
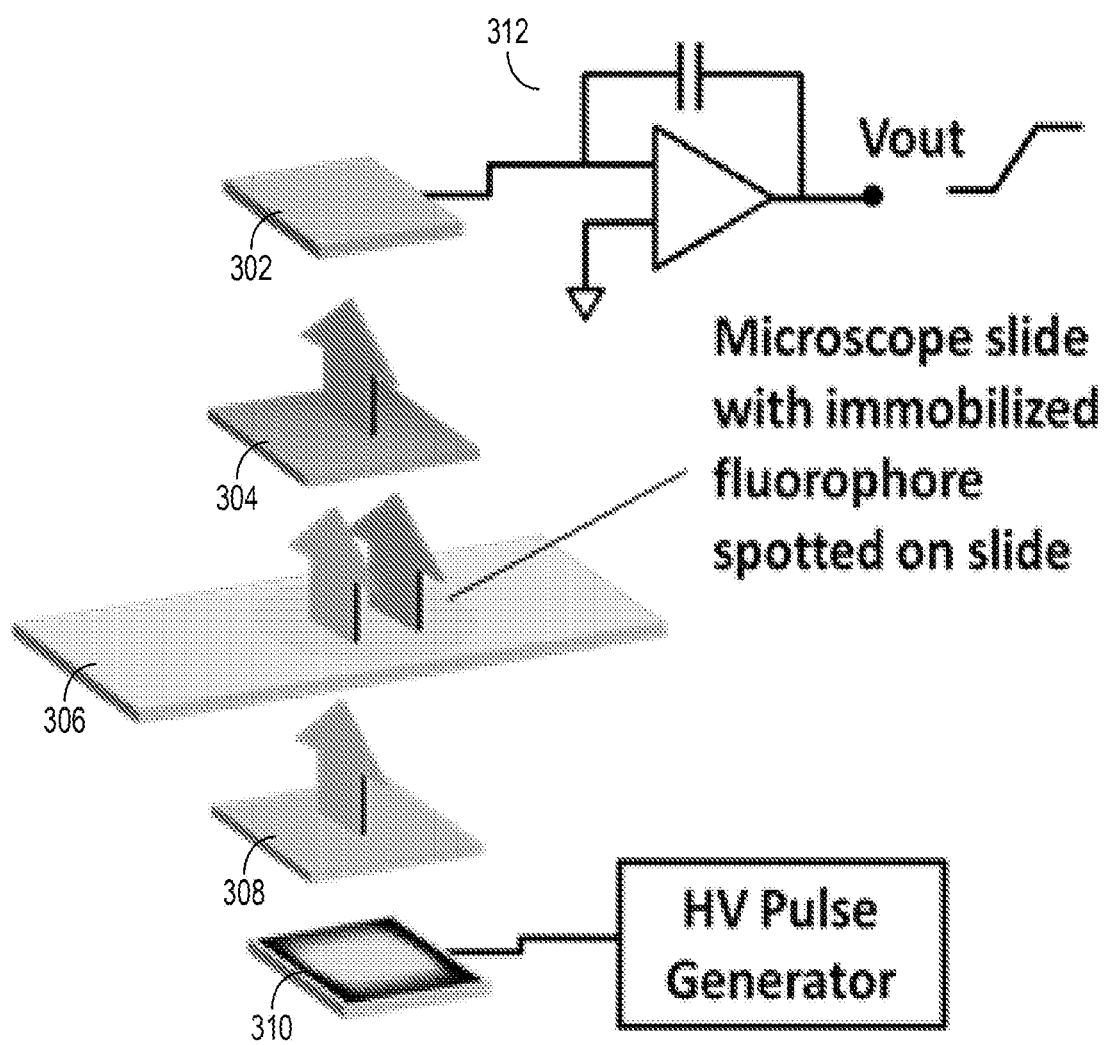
FIG. 3 is a schematic depicting the structure of an example system implemented according to the present application.

Referring to FIG. 1 again, after a layered structure is assembled in step 104, in step 106, light emitted from the immobilized fluorophores in the slide 306 is detected by the photodiode detector 302 that generates currents in response to the light. In step 108, the output current of the photodiode detector is connected to a circuit (e.g., a low-noise charge integration circuit 312 as shown in FIG. 3) and converted to a relatively-large output voltage. In step 110, the ramp time that depicts how quickly the detected optical signal ramps form one voltage to another is measured. In some embodiments, an operational amplifier in the circuit can be powered on and off to start and stop the voltage ramp, respectively. In step 112, the ramp time is used to determine the fluorophore concentration on the microscope slide. The ramp time Δt is expressed by the following relation:

$$i = C\Delta V/\Delta t \quad (1),$$

where i is the current detected by the photodiode detector, C is the concentration of the fluorophores, and ΔV is the voltage ramp.

Figure 5:
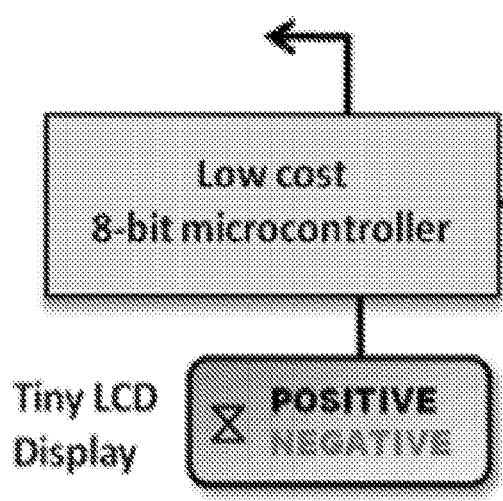
FIG. 5 is a schematic depicting the structure of an example point-of-care optical biosensor system implemented according to the present application. As described herein, charge integration enabled accuracy approaching state-of-the-art clinical laboratory instrumentation.
Figure 5:
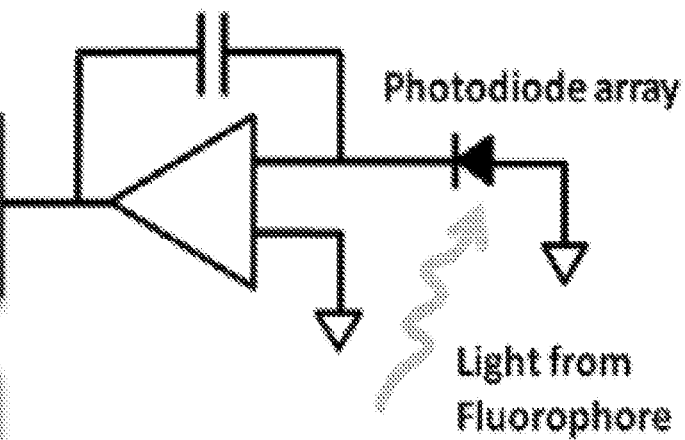

As described in equation 1, the fluorescent signal is reported as output voltage ΔV, which is stored by integrating capacitor C. When more (orange) fluorophores are captured on the antibody biorecognition site, the detected signal ramps faster and reaches the voltage rail in a shorter period of time due to the higher current i detected by the photodiode. For sample analysis, the ramp time Δt, is now inversely proportional to the concentration of the fluorescently labeled Ab biomarker in the patient sera. This provides the desired quantitative relationship between analyte concentration and the detected output. The primary advantage of this system is the ability to use long op-amp charge integration times (30 to 60 seconds) to detect extremely low light levels from a very small number of fluorophores captured on the biorecognition site, by providing a robust electrical signal (output voltage) to help separate out the detected and extremely weak fluorophore signal from the background noise level. The microcontroller then translates the detected voltage signal into quantitative information provided on a small integrated display. While previous research has evaluated using lock-in amplifier technology to detect the very low signal (light) levels from the excited fluorophores to improve sensitivity [3], for very low-cost and ultimately disposable point-of-care applications, a much less costly electronics detection method is required. Initially, we evaluated a very high gain Op Amp-based transimpedance amplifier circuit, but we found the low picoamp signals at the lower fluorophore concentrations were challenging to detect using low-cost electronic components. As a solution, we recognized that for this particular application, real-time instantaneous detection was not necessary. Instead, we exploit a tradeoff between detection time and accuracy with a simple, low-cost charge integration Op Amp-based circuit, where longer integration time translates to higher sensitivity. For example, it may be advantageous to use a charge integration Op Amp-based circuit configuration illustrated in FIG. 5. This configuration is particularly advantageous for disposable, point-of-care applications where cost of the detection method is a significant consideration. We observed charge integration times between 30 seconds and one minute worked well to detect the lower fluorophore dilutions and helped separate out the fluorophore signal from the background control level.

Figure 4:
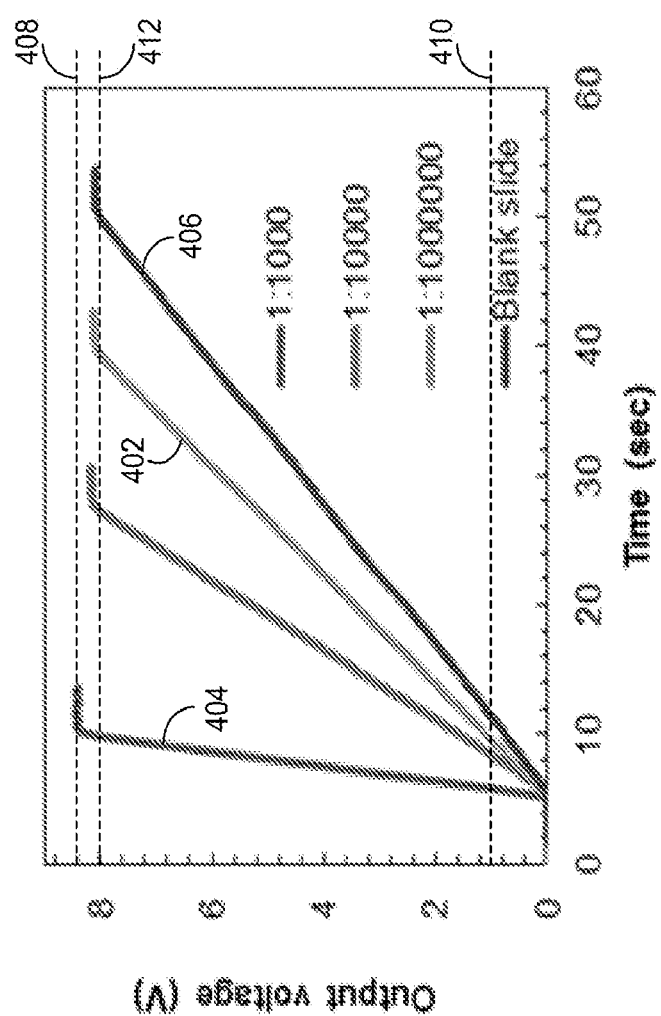
FIG. 4 is a plot of output voltage of an example system versus time.

Referring to FIG. 4, an example plot of voltage output for three concentrations of 1 μm diameter Nile Red (520 Ex/570 Em) fluorescent microspheres immobilized on microscope slides using a green OLED emitter is provided. The blank slide plot (line 406) represents the optical noise floor of the system with the green OLED turned on. As the immobilized fluorophore dilution is decreased from 1:1000000 (line 402) to 1:1000 (line 404), the detected output voltage ramps faster and reaches the voltage rail in a shorter period of time due to the higher current i detected by the photodiode, which is due to more immobilized fluorophores. That is, how fast the output voltage ramps to the supply voltage rail—i.e., the inverse of the ramp time—is proportional to the fluorophore concentration. The ramp time can be measured with an oscilloscope by sending the output voltage from circuit 312 (shown in FIG. 3) to the oscilloscope. The ramp time can be measured as the time interval that the output voltage takes to ramp from 0 volt to when the output voltage reaches the maximum voltage output or the supply voltage rail (shown by line 408). In one configuration, the ramp time can be measured as the time interval that the output voltage takes to ramp from one voltage (shown by line 410) to a different voltage (shown by line 412).

The systems and methods as disclosed herein can use long op-amp charge integration times (e.g., 30 to 60 seconds) to detect extremely low light levels from a very small number of fluorophores captured by the primary on the microscope slide, separate the detected weak fluorophore signals from the background level, and in turn provide clinical-level sensitivity. Also, the systems and methods as disclosed herein provide a wide dynamic range of detection that is essential in further increasing their sensitivity and quantitative abilities.

Referring again to FIG. 1, after step 112 where the concentration of the fluorophores is determined, a general range of biomarker concentration can be derived because fluorophores are bound to the biomarkers. Thus, a report regarding the biomarkers is generated afterwards in step 114. For example, being positive (+) or negative (−) the biomarkers is indicated in the report based on 3 standard deviations of the mean of the controls. Clinicians and healthcare workers can use the quantitative information in the report to monitor a patient's progress to a specific therapeutic regimen or identify the severity or stage of a patient's disease.

Using the systems and methods as disclosed herein, in comparison to a prior method of RAPID ELISA, 100% accuracy can be achieved with a higher confidence level than the prior method. Also, the systems and methods as disclosed herein have a wide dynamic range to demonstrate the quantitative relation between the biomarker (e.g., HPV16 E7 antibody) concentration and the detected output signals.

Figure 6:
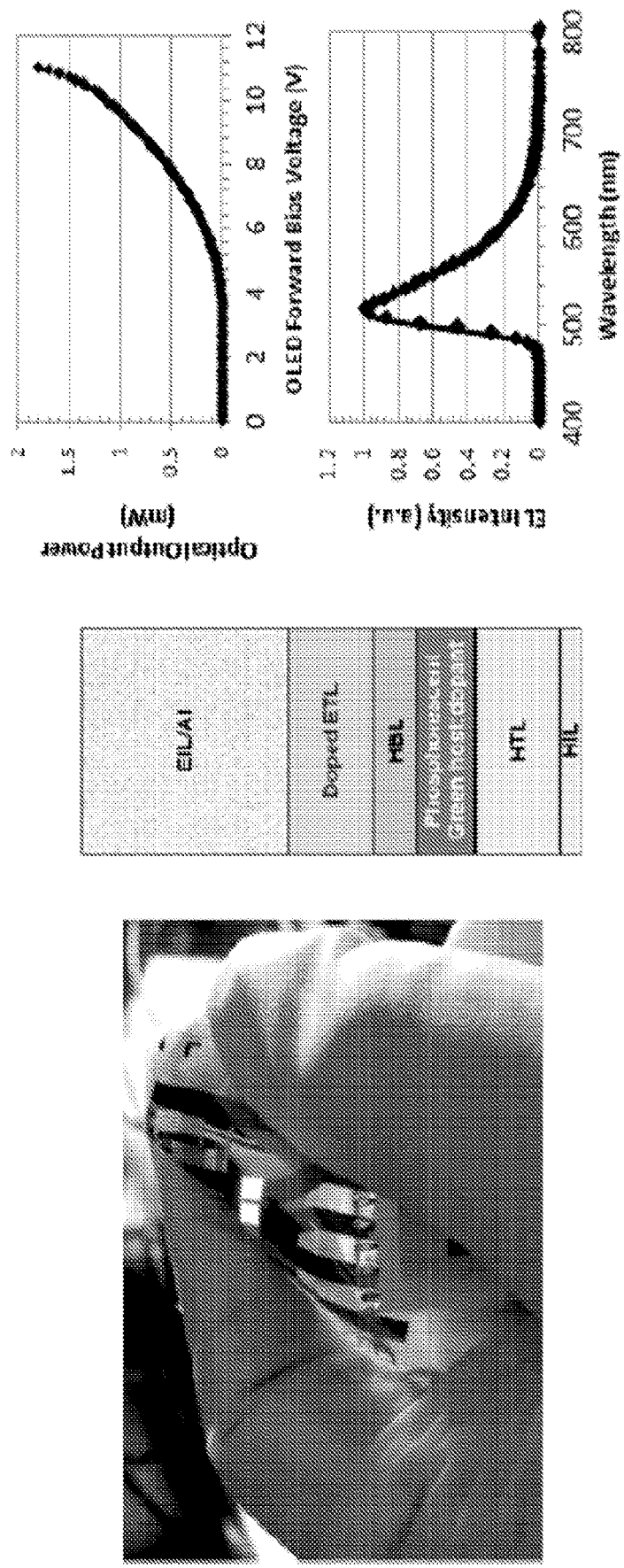
FIG. 6 demonstrates a flexible high intensity green OLED device structure. A flexible 5 mm² bottom emitting green OLED display test structure was used for this work. Detailed phosphorescent green OLED device structure, with scaled organic layer thicknesses. Optical output is shown for the green OLED test structure and the Electroluminescence (EL) spectra.
Figure 7:
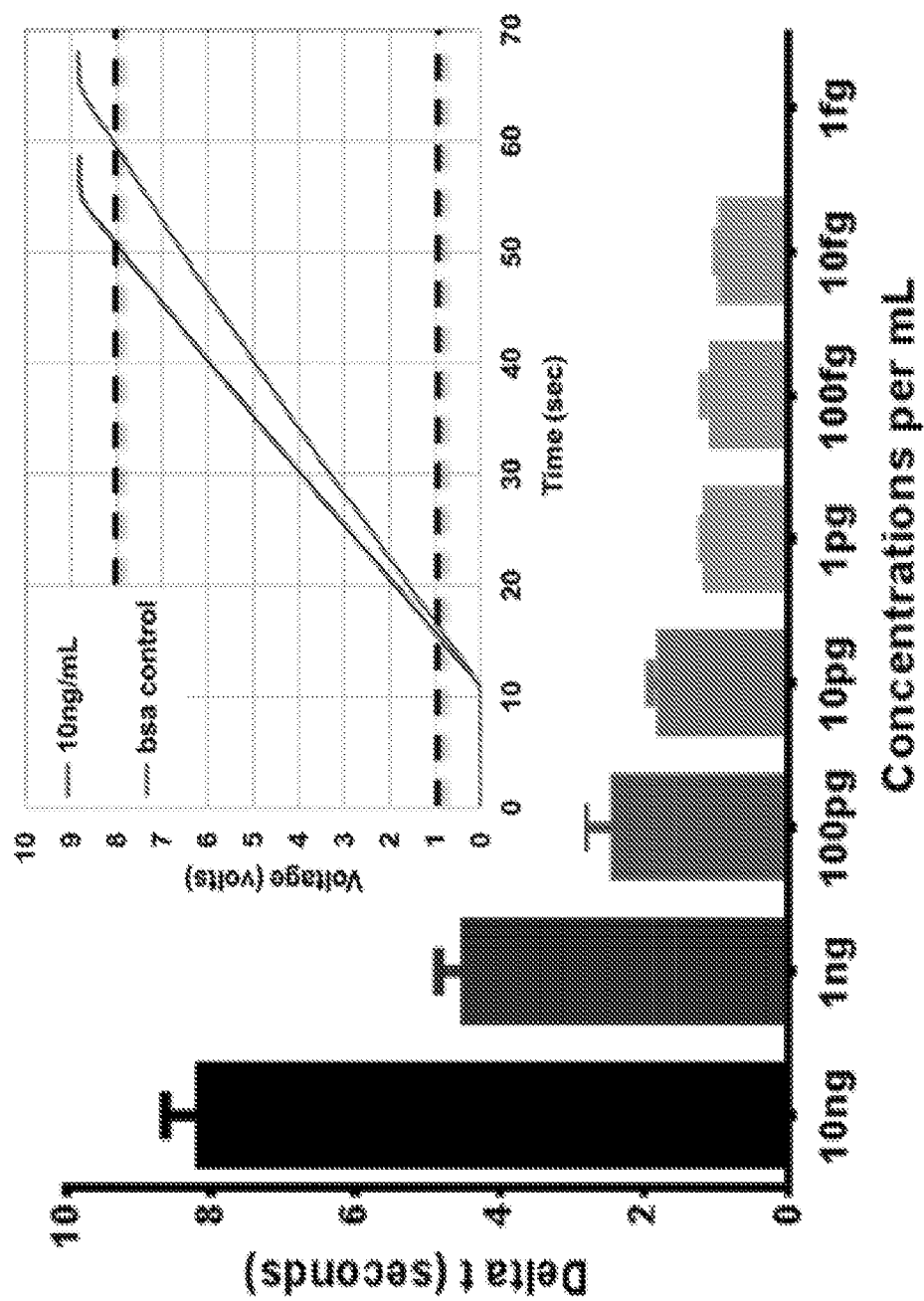
FIG. 7 presents ELISA assay data of the detection of whole human IgG by fluorescent biorecognition. Dylight 549 anti-human fluorophores bound to the whole human IgG are excited by a green OLED and the emitted orange light is quantified. From the inset plot, signal output is determined by the ramp time (sec), which is the time from 1 to 8 volts. The difference in ramp time (or time to reach threshold) between our sample and a BSA control quantifies concentration as delta t, demonstrating a conservative lower-limit-of-detection of 10 pg/mL.

In another aspect, deposition of thin-film organic and inorganic OLED layers can performed using an OLED deposition tool from SUNIC Systems. For example, a green OLED device structure is illustrated in FIG. 6, comprising injection, transport, and blocking layers, along with the emission layer. These layers are abbreviated as HIL (hole injection layer), HTL (hole transport layer), HBL (hole blocking layer), ETL (electron transport layer), and EIL (electron injection layer). In some cases, a reflective aluminum layer is used to form the cathode, and the anode is a transparent indium tin oxide (ITO) layer located directly under the HIL. A phosphorescent host dopant system can be used as the emissive layer, where the injected electrons and holes recombine to emit the (bright) green 515 nm light.

EXAMPLES

Example 1—Demonstrating Fluorescent Immunoassay for the Detection of Serum HPV16 E7 Antibodies Point-of-care molecular diagnostics can provide efficient and cost-effective medical care, and have the potential to fundamentally change our approach to global health. However, most existing low cost approaches are unable to scale to multiple biomarkers and only offer analytical sensitivity in the ng/mL range. As a solution, we have combined low cost commercial flat panel OLED display technology with protein microarray technology to enable high density fluorescent, programmable, multiplexed biorecognition in a compact and disposable configuration with clinical level sensitivity. Our approach leverages advances in commercial display technology to reduce pre-functionalized biosensor substrate costs to pennies per cm$^2$. Here, we demonstrate quantitative detection of IgG antibodies to multiple viral antigens in patient serum samples with detection limits for human IgG in the 10 pg/mL range. We also demonstrate multiplexed detection of antibodies to the HPV16 proteins E2, E6, and E7, which are circulating biomarkers for cervical and head and neck cancers, with 100% correlation to our current laboratory-based measurement instrumentation.

HPV infection is the most commonly diagnosed sexually transmitted disease in the United States [32]. Infection with high-risk HPV is necessary for cervical cancers (99.7%) as well as the majority of oropharyngeal head and neck squamous cell carcinoma (65-80%) [11]. While screening by a combination of cytology and high-risk HPV typing has markedly decreased cervical cancer incidence in developed countries, there is a need for accurate and low-cost point-of-care assays for the biologic changes that are associated with progression of HPV infection to HPV cancer [32]. Previously, we and others have reported that HPV16 E2, E6, and E7 IgG antibodies are specifically detected in the sera of patients with HPV-associated cancers ([8, 33] and unpublished observations). Here, we have adapted the Rapid Antigenic Protein In Situ Display (RAPID) ELISA immunoassay [8, 15, 16] for the serological detection of HPV16 E7 antibodies using OLED-based fluorescent detection of human IgG. To demonstrate the accuracy, specificity, and inter- and intra-assay reproducibility of the optical configuration, we generated full-length recombinant HPV16 E7 protein and manually spotted pitch-matched HPV16 E7, BSA and whole-human IgG protein onto aminosilane coated glass microscope slides. The slides were blocked in 5% milk in 0.2% PBS-Tween20 followed by incubation with patient sera. We then determined the presence of IgG antibodies against HPV16 E7 by probing the slide with fluorescent anti-human IgG Dylight 549 antibody and measured the relative fluorescence. Using monoclonal antibodies against HPV16 E7, the immobilization of HPV16 E7 recombinant protein was confirmed (FIG. 8A, anti-HPV16 E7).

We immobilized 25 μg/mL of recombinant HPV16 E7 protein and determined the optimal signal-to-noise ratio by diluting serum from a previously identified subject with high titers of IgG antibodies specific for HPV16 E7 (HPV16 E7 IgG Positive) and serum from a healthy control (HPV16 E7 IgG Negative) (FIG. 8A). Dilutions of sera at 1:4, 1:40 and 1:200 in 5% milk-PBST were added and determined the delta t (sec) value for replicated samples. As illustrated in FIGS. 8A-8B, day 1, even at a 1:4 dilution (comparable to the volume from a finger-prick point-of-care immunoassay) we observe only low levels of off target fluorescent signal. We replicated the assay using the same sera at a 1:4 dilution over four consecutive days, and calculated the intra-assay variability represented by the standard error of the mean in duplicate samples each day. The intra-assay variability remained low and is representative of current standards for diagnostic assays (FIG. 8B). The inter-assay variability is shown as the coefficient of variance (CV) over the four-day period (FIG. 8C). Current analytic targets for inter-assay variability are below a CV value of 20% [34, 35]. The observed CV values were 13% for E7-specific IgG antibodies. We have observed that variations in inter- and intra-assay variability are often introduced in the printing process. We expect that as transitioning the printing process from manual spotting to a contact or piezo printer at high batch volume will reduce spot size variability and further improve inter- and intra-assay variability.

Figures 9A, 9B:
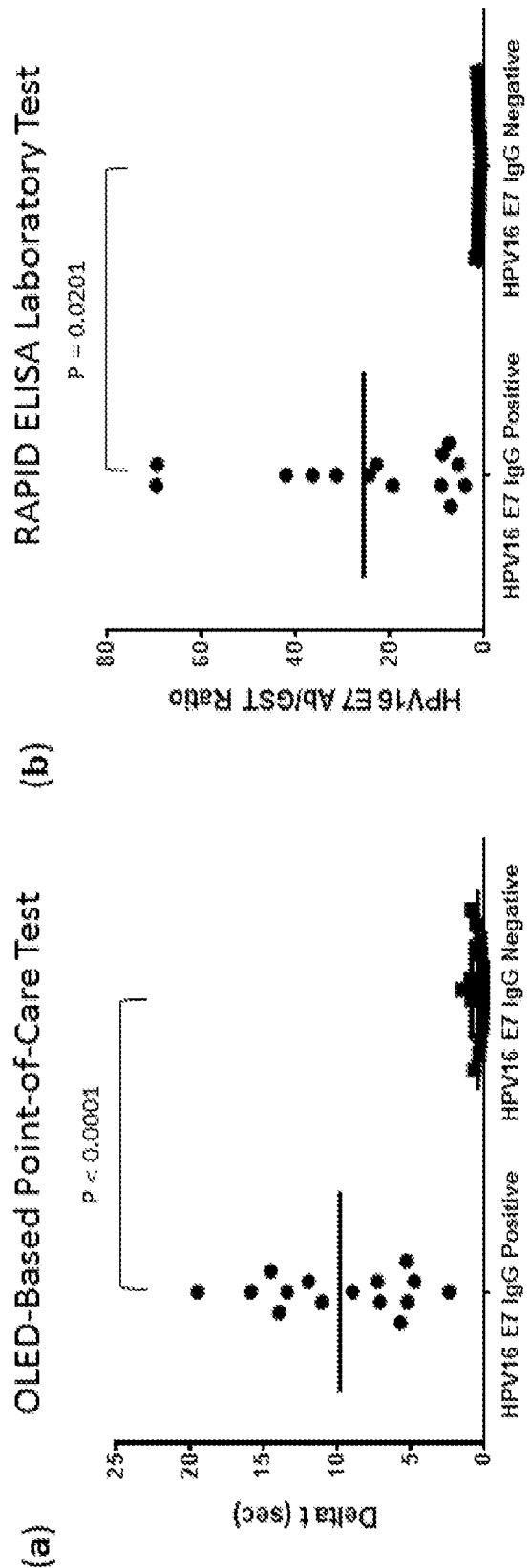
FIGS. 9A-9B present plots of (a) OLED-based point-of-care test configuration against our previously reported (b) RAPID ELISA assay. OLED-based configuration demonstrated similar accuracy and specificity as RAPID ELISA laboratory test instrumentation. Sera from 15 subjects known to contain HPV16 E7 antibodies and sera from 15 subjects known to be negative for HPV16 E7 antibodies were evaluated for HPV16 E7-specific IgG.

To determine the accuracy and specificity of the HPV16 E7 immunoassay, 25 μg/mL of recombinant HPV16 E7 protein was immobilized, and sera from patients with oropharyngeal cancer were screened for the presence of serum antibodies against HPV16 E7 using our RAPID ELISA immunoassay [33]. We selected 30 serum samples, 15 sera known to be positive for HPV16 E7 IgG antibodies and 15 negative for HPV16 E7 IgG antibodies in duplicate on individual slides. We determined a cutoff value as the mean of the controls+3 standard deviations for each assay (OLED-Based Point-of-Care Test, 1.74; RAPID ELISA, 1.86). Using this cutoff value, the OLED point-of-care assay detected the HPV16 E7 IgG in all 15 cases and no controls, comparable to the laboratory-based RAPID ELISA test (FIGS. 9A-9B).

Figures 10A, 10B:
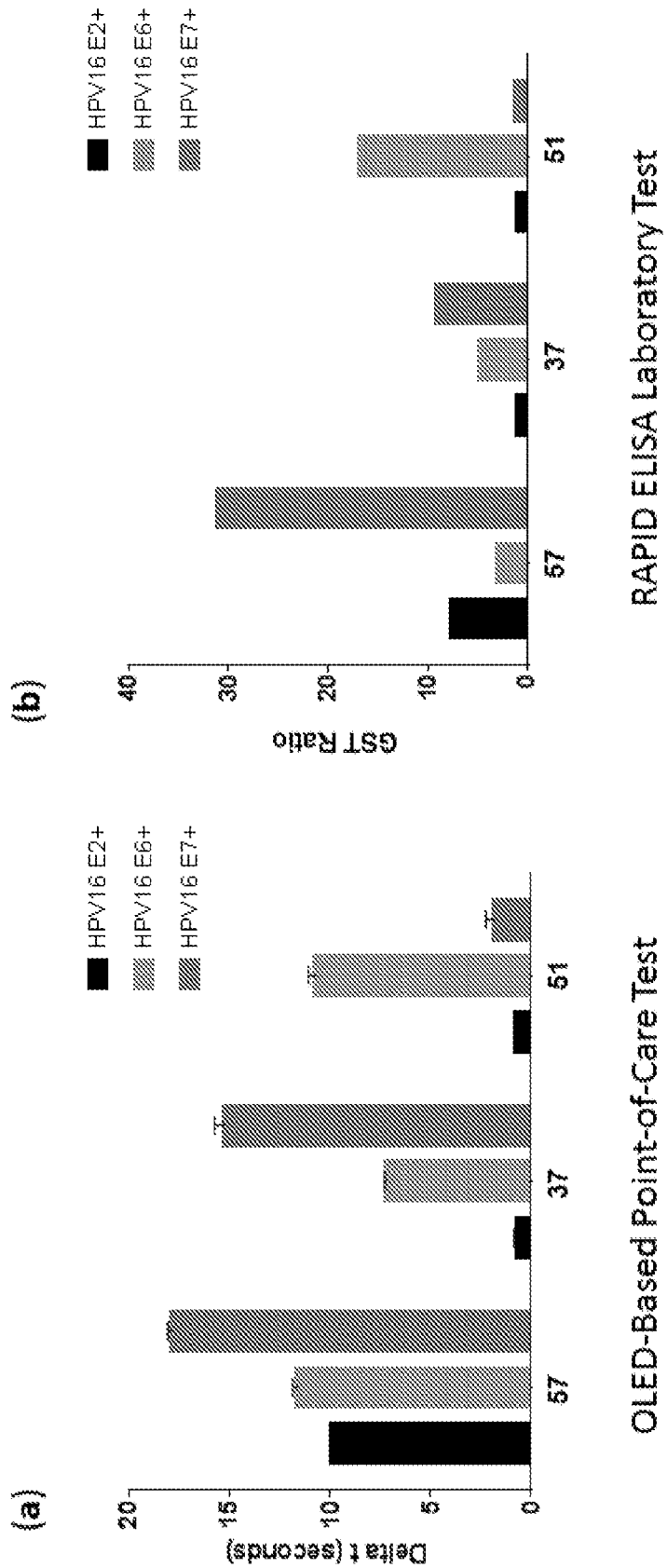
FIGS. 10A-10B demonstrate multiplexed detection of human IgG in patient sera. To evaluate the detection of multiple biorecognition sites we immobilized recombinant HPV16 E2, E6 and E7 protein as well as human IgG and BSA at 6 mm intervals. Serum from three patients with known serum antibodies to all or one of the HPV16 proteins was selected and (a) compared the results of our OLED-based point-of-care test configuration against our previously reported (b) RAPID ELISA assay measuring human IgG in the same serum samples. Results demonstrated comparable detection results to multiple serum antibodies for each of the three patients using our prototype test configuration to the RAPID ELISA diagnostic laboratory test.

In our previous study, we analyzed the utility of a multi-antigenic assay for the detection of patients with HPV16 positive oropharyngeal head and neck cancer [8]. The majority of patients were positive for HPV16 E1, E2, E6, and/or E7 antibodies. A case was determined positive by the presence of one or more positive antibodies. In this study, over 5% of patients with oropharyngeal head and neck cancer have antibodies to HPV16 E1 or E2, but no E6 or E7 antibodies. Using a multiparametric algorithm the sensitivity approaches 88% at 96% specificity. This supports the rationale for a multi-antigenic assay for the early detection of HPV positive oropharyngeal head and neck cancer. To demonstrate the preliminary ability of our OLED-based point-of-care biosensor configuration to detect multiple biorecognition sites, we immobilized 25 μg/mL of recombinant HPV16 E2, E6, E7, whole human IgG, and BSA on five separate ~2 mm diameter biorecognition sites spaced at 6 mm intervals on the same microscope slide and compared our point-of-care test configuration results with our RAPID ELISA laboratory test results. The five sites were detected using the singleplex prototype test configuration (FIG. 3) by simply incrementing (pulling) the slide 6 mm out at a time to sequentially line up the sites with the center of the ~2 mm green OLED emitter. This approach provided a simple, but effective early demonstration of multiplexing performance using just a single emitter. For the multiplexed comparison, we selected three sera from OPC patients, previously identified through our custom RAPID ELISA assay as being positive for IgG antibodies against HPV16 E2 and E7 (57), HPV16 E6 and E7 (37), and HPV16 E6 (51) proteins. As illustrated in FIGS. 10A-10B, we detected multiple serum antibodies for each of the three patients using our prototype OLED-based point-of-care test configuration, comparable to the RAPID ELISA laboratory test. We observed increased detection of the HPV16 E6 antibody in patient 57 using our OLED-based point-of-care test configuration compared to our previously reported RAPID ELISA laboratory test that is likely due to differences in antigen display between the two assays. This demonstrated that the OLED-based point-of-care test configuration can be used to specifically detect individual bound IgG without evidence of cross-over interference, as well as provide comparable detection results to the RAPID ELISA laboratory test to multiple serum antibodies.

Figures 11A, 11B:
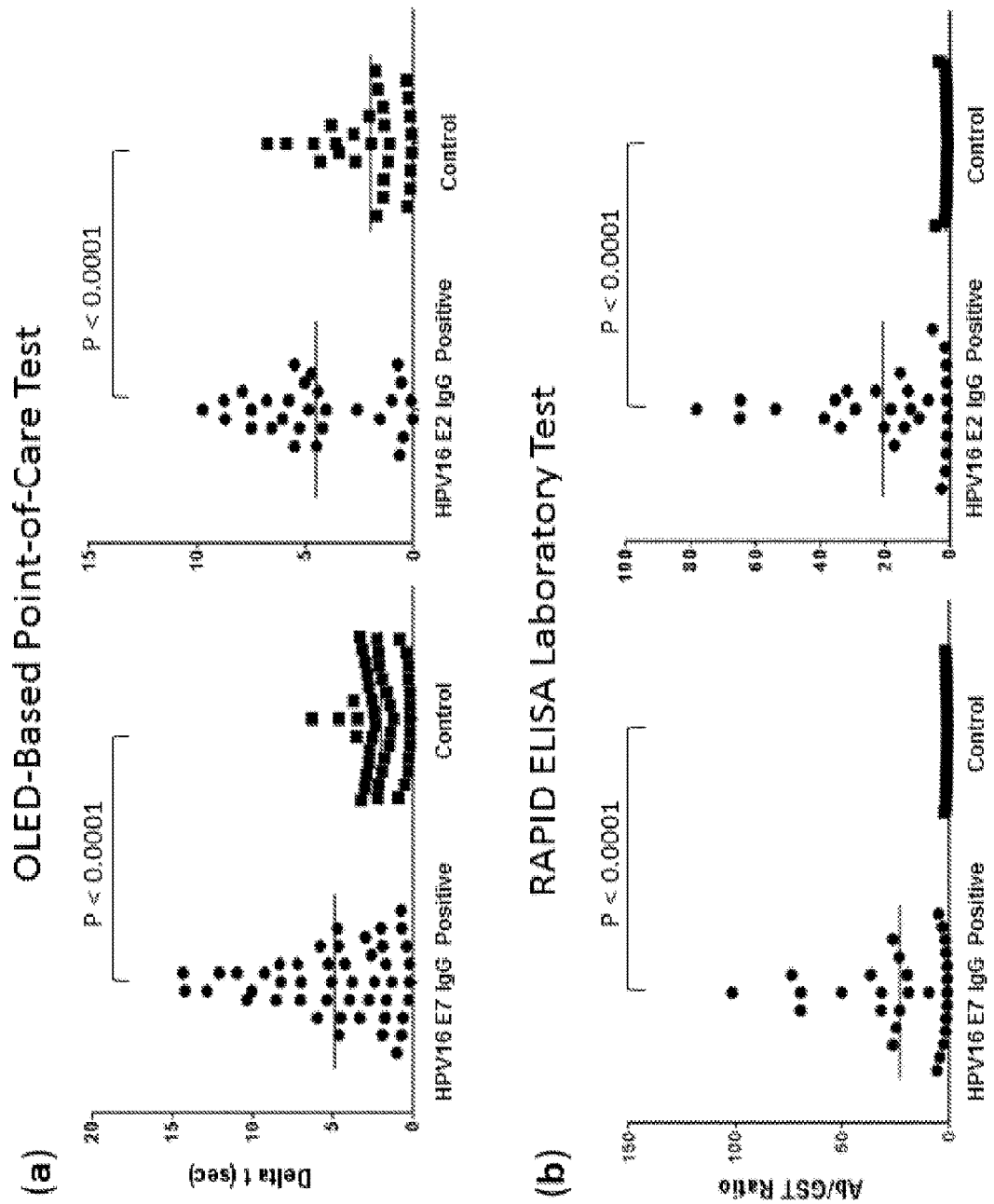
FIGS. 11A-11B present a comparison of OLED POC assay to Rapid ELISA laboratory test for multiplexed detection of human IgG in patient sera. Sera from 32 HPV16+ patients and 39 healthy controls were evaluate the detection of HPV16 E2 and E7 specific IgG. The results of the (a) OLED-based point-of-care test configuration against our previously reported (b) RAPID ELISA assay are shown. OLED-based configuration demonstrated sensitivity of 59% at 95% specificity using a cutoff value of the mean of the controls+2 standard deviations compared to our previously reported RAPID ELISA laboratory test instrumentation with a sensitivity of 83% at 95% specificity. Significance was determined using a student's t-test.

To determine the accuracy and specificity of the HPV16 multiplexed immunoassay, we immobilized 25 ug/mL of recombinant HPV16 E7, E2, whole human IgG, and BSA on five separate ~2 mm diameter biorecognition sites spaced at 6 mm intervals on a glass microscope slide. We randomly selected 32 HPV16+serum samples as well as 39 healthy controls from our previously reported HOTSPOT study and screened them in duplicate on individual slides[14]. The 5 sites were detected as described above by incrementally pulling out the slide 6 mm at a time to line up the sites with the center of the green OLED emitter. We determined a cutoff value as the mean of the controls+2 standard deviations for each HPV antigen (OLED-Based Point-of-Care Test, HPV16 E7, 4.680; E2, 4.246; RAPID ELISA, HPV16 E7, 1.647; E2, 2.663). Using this cutoff value, the overall sensitivity and specificity defined as a case or control being positive for one or more HPV antigen (HPV16 E2 and/or E7) was 58% sensitivity at 95% specificity for the OLED-Based Point-of-Care test compared to 83% sensitivity at 95% specificity for the RAPID ELISA laboratory test (FIGS. 11A-11B). These results were comparable if not better, for HPV16 E2 and E7, to our RAPID ELISA laboratory test.

In this report, we have demonstrated the novel combination of commercial flat panel OLED display technology with high density fluorescent biorecognition microarray technology to fabricate a prototype point-of-care immunoassay. Our results demonstrate a wide dynamic range and high diagnostic sensitivity approaching 10 pg/mL for human IgG, surpassing the current limits of detection in traditional lateral flow immunoassays and approaching the limits of detection observed in clinical diagnostic laboratories. In comparison to a well-established laboratory ELISA, we have demonstrated a similar accuracy and specificity in the detection of serum antibodies against HPV16 E7, a potential blood-based biomarker under evaluation for cervical and oropharyngeal head and neck cancer detection. Further, we present data supporting the multiplexed detection of serum antibodies with minimal signal interference.

Point-of-care medical diagnostic sensors have the potential to reduce health care costs by rapid feedback on disease states. Current point-of-care disposable immunodiagnostics are primarily paper-based colorimetric lateral flow immunoassays that provide a narrow dynamic range of detection and sensitivities in the ng/mL range [36]. Advances in wearable and flexible sensor development, specifically in OLED and organic photodetectors provide a novel avenue to combine fluorescent planar array technology providing a low-cost, highly sensitive diagnostic device. While the work in this manuscript has focused on the detection of antibodies specific for HPV proteins, the programmable molecular and electronic configuration presented provides many opportunities to adapt this system to meet the demands of multiple types of analytes and clinical applications.

Methods

Serum samples: Serum samples were previously obtained at the time of clinical diagnosis from patients with newly-diagnosed HPV+ oropharyngeal cancer and healthy controls and the serologic responses to HPV16 have been previously reported [33] (Clinical Trials number: NCT01342978). Written informed consent was obtained from all subjects under institutional review board approval.

HPV Antibody Detection in Blood Sample by RAPID ELISA:

Serum samples (1:100) were tested for HPV16 E2, E6 and E7 IgG antibodies by programmable RAPID ELISA as previously described [15]. Proteins were expressed using a human HeLa cell lysate in vitro transcription and translation system (Thermo Scientific) and blocked with 10% *Escherichia coli* (*E. coli*) lysate. Luminescence was measured as Relative Light Units (RLU) as a ratio to GST-antigen control. Cut-off values for positive serology are defined as the mean+3 standard deviations of the RLU ratio observed among the healthy controls.

Expression and Purification of HPV16 E2, E6, and E7:

pDEST15 (Life Technologies) was used to generate N-terminal Glutathione transferase fusion proteins. E2 protein was subcloned as the C-terminal fragment (CE2) for optimal protein expression [8]. E6, E7 and CE2 genes in the vector pDONR221 were transferred to the destination vector pDEST15 by recombination cloning and transformed into the BL21DE3 *E. coli* strain. Isolated colonies were grown in LB media for 6-8 hr at 37° C. The cultures were then diluted 1:20 into LB media and grown at 37° C. until OD600 of 0.6 was reached and induced with IPTG at 18° C. for 21 hr. After 21 h incubation at 18° C., the bacteria were centrifuged at 5000×g for 20 min at 4° C., and the pellets were resuspended in lysis buffer (50 mM Potassium phosphate, pH 7.8, 400 mM NaCl, 100 mM KCl, IGEPAL 0.01%, 1 mM DTT, 25 µg/ml DNase, 2 mg/ml Lysozyme, 5 mM $MgSO_4$, 100 µM PMSF). The lysate was frozen at −20° C., then thawed to RT and mixed for 1 hr at 37° C. The lysate was centrifuged at 5000×g for 20 minutes at 4° C. and the supernatant was removed and mixed with Glutathione Sepharose 4 fast flow medium and allowed to bind O/N at 4° C. Glutathione Sepharose medium was washed seven times with PBS pH 7.3 by centrifugation at 500×g for 5 min. Elution buffer (Tris HCl pH 8 containing 20 mM GSH) was used to elute GST tagged proteins and a Bradford assay was used to quantitate the protein. Purity of proteins was determined by Sodium dodecyl sulfate (SDS) Poly acrylamide gel electrophoresis (PAGE).

Fluorescent Detection of Human Serum IgG Using a Point of Care Configuration:

As illustrated in [8], glass microscope slides (VWR International) were coated in a 2% aminosilane coating solution (Pierce) for 15 minutes at room temperature. The slides were then rinsed with acetone followed by distilled water and dried with filtered compressed air. Purified recombinant protein was diluted in distilled water to 25 µg/mL and spotted (5 µl) on the aminosilanated glass slides and allowed to dry at room temperature. As a control, bovine serum albumin (BSA) was diluted in distilled water to 25 µg/mL and spotted (5 µl) on separate aminosilanated glass slides and allowed to dry at room temperature. The protein spotting procedure was repeated four times. The slides were stored at 4° C. overnight. Slides were washed once in phosphate buffered saline pH 7.4-0.2% Tween20 (PBST) solution and blocked at room temperature in 5% milk-PBST for one hour.

During the blocking step the serum samples were diluted 1:1 in a 5% milk-PBST and allowed incubate at room temperature. The slides were then removed from the blocking solution and incubated with the serum for 1 hour at room temperature and then rinsed once in PBST. The presence of human IgG antibodies specific for the recombinant proteins was detected using Dylight 549-conjugated AffiniPure Goat Anti-Human IgG (Jackson ImmunoResearch Laboratories, Inc.). As a positive control we probed the purified HPV16 E7 recombinant protein with a mouse monoclonal antibody to HPV16 E7 (Santa Cruz) and detected it with anti-mouse IgG AlexaFluor 555 (Life Technologies).

Statistical Considerations:

OLED based point-of-care and RAPID ELISA laboratory analysis were performed in duplicate. Significant differences (p-value) in cases and controls were assessed by two-tailed student t-test. To assess the value of AAb to discriminate cases from controls we defined the cut-off value as the mean of the controls+3 standard deviations.

OLED Fabrication and Characterization:

The OLED devices used in this work were fabricated on previously patterned indium-tin oxide (ITO) substrates. The device structure consisted of a 10 nm layer of hexaazatriphenylene hexacarbonitrile (HAT-CN) hole injection layer (HIL), followed by a 40 nm 4-4'-bis[N-(1-naphthyl)-N-phenyl-amino]biphenyl (NPD) hole transport layer (HTL). A 10-50 nm green emissive layer (EML) was deposited onto the HTL and comprised a co-host structure of [Host1:Host2:Green dopant]. Next, a 10-30 nm thick hole blocking layer (HBL) was deposited onto the EML, followed by a 30 nm electron transport layer (ETL) consisting of doped 8-hydroxyquinolinolato-lithium (Liq). A 2 nm Liq electron injection layer (EIL) was deposited onto the ETL, followed by a 100 nm layer of MgAg or Al cathode metal. Device area was 0.05 $cm^2$. Films were deposited by vacuum thermal evaporation in a Sunicel Plus 400 system made by Sunic Systems (Suwon, Korea) at pressures below $5\times10^{-7}$ Torr. Films were patterned using metal shadow masks with no break in vacuum between layers. The devices were encapsulated using a thin-film barrier material from 3M Company. HAT-CN was purchased from Lumtec (Hsin-Chu, Taiwan) and the other organic materials were supplied by Universal Display Corporation (New Jersey, USA).

Encapsulated devices were tested in ambient conditions. Current density/voltage, radiance and electroluminescence measurements were made using a Keithley 2400 source meter, calibrated Si photodiode model 818-UV from Newport (Irvine, Calif., USA) and Ocean Optics HR-4000 spectrometer, using Spectra Suite software (Ocean Optics, Dunedin, Fla., USA).

REFERENCES

[1] M. E. Porter, "What is value in health care?," *N Engl J Med*, vol. 363, pp. 2477-81, Dec. 23, 2010.

[2] J. H. Nichols, "Reducing medical errors at the point of care," *Laboratory Medicine*, vol. 36, pp. 275-277, May 2005.

[3] A. St John and C. P. Price, "Economic Evidence and Point-of-Care Testing," *Clin Biochem Rev*, vol. 34, pp. 61-74, August 2013.

[4] P. J. Tighe, R. R. Ryder, I. Todd, and L. C. Fairclough, "ELISA in the multiplex era: potentials and pitfalls," *Proteomics Clin Appl*, vol. 9, pp. 406-22, April 2015.

[5] M. D. Perkins and M. Kessel, "What Ebola tells us about outbreak diagnostic readiness," *Nature Biotechnology*, vol. 33, pp. 464-469, May 2015.

[6] M. Cretich, F. Damin, and M. Chiari, "Protein microarray technology: how far off is routine diagnostics?," *Analyst*, vol. 139, pp. 528-42, Feb. 7, 2014.

[7] M. J. Broadhurst, J. D. Kelly, A. Miller, A. Semper, D. Bailey, E. Groppelli, et al., "ReEBOV Antigen Rapid Test kit for point-of-care and laboratory-based testing for Ebola virus disease: a field validation study," *Lancet*, Jun. 25, 2015.

[8] K. S. Anderson, J. Wong, G. D'Souza, A. B. Riemer, J. Lorch, R. Haddad, et al., "Serum antibodies to the HPV16 proteome as biomarkers for head and neck cancer," *Br J Cancer*, vol. 104, pp. 1896-905, Jun. 7, 2011.

[9] C. Desmetz, A. Mange, T. Maudelonde, and J. Solassol, "Autoantibody signatures: progress and perspectives for early cancer detection," *J Cell Mol Med*, vol. 15, pp. 2013-24, October 2011.

[10] J. W. Pedersen, A. Gentry-Maharaj, E. O. Fourkala, A. Dawnay, M. Burnell, A. Zaikin, et al., "Early detection of cancer in the general population: a blinded case-control study of p53 autoantibodies in colorectal cancer," *Br J Cancer*, vol. 108, pp. 107-14, Jan. 15, 2013.

[11] C. A. Moody and L. A. Laimins, "Human papillomavirus oncoproteins: pathways to transformation," *Nat Rev Cancer*, vol. 10, pp. 550-60, August 2010.

[12] A. Goodman, "HPV testing as a screen for cervical cancer," *Bmj-British Medical Journal*, vol. 350, Jun. 30, 2015.

[13] K. S. Anderson, K. R. Dahlstrom, J. N. Cheng, R. Alam, G. J. Li, Q. Y. Wei, et al., "HPV16 antibodies as risk factors for oropharyngeal cancer and their association with tumor HPV and smoking status," *Oral Oncology*, vol. 51, pp. 662-667, July 2015.

[14] K. S. Anderson, N. Ramachandran, J. Wong, J. V. Raphael, E. Hainsworth, G. Demirkan, et al., "Application of Protein Microarrays for Multiplexed Detection of Antibodies to Tumor Antigens in Breast Cancer," *Journal of Proteome Research*, vol. 7, pp. 1490-1499, 2008 Apr. 1, 2008.

[15] K. S. Anderson, J. Wong, A. Vitonis, C. P. Crum, P. M. Sluss, J. Labaer, et al., "p53 autoantibodies as potential detection and prognostic biomarkers in serous ovarian cancer," *Cancer Epidemiol Biomarkers Prev*, vol. 19, pp. 859-68, March 2010.

[16] N. Ramachandran, A. K S, J. Raphael, E. Hainsworth, S. Sibani, W. Montor, et al., "Tracking humoral responses using self assembling protein microarrays," *Proteomics-Clinical Applications*, vol. 2, pp. 1518-1527, 2008.

[17] L. Lee, E. Nordman, M. Johnson, and M. Oldham, "A Low-Cost, High-Performance System for Fluorescence Lateral Flow Assays," *Biosensors*, vol. 3, pp. 360-373, 2013.

[18] A. Pais, A. Banerjee, D. Klotzkin, and I. Papautsky, "High-sensitivity, disposable lab-on-a-chip with thin-film organic electronics for fluorescence detection," *Lab Chip*, vol. 8, pp. 794-800, May 2008.

[19] G. Ryu, J. Huang, 0. Hofmann, C. A. Walshe, J. Y. Sze, G. D. McClean, et al., "Highly sensitive fluorescence detection system for microfluidic lab-on-a-chip," *Lab Chip*, vol. 11, pp. 1664-70, May 7, 2011.

[20] R. Dixit, S. Li, M. Ratterman, I. Papautsky, and D. Klotzkin, "Simultaneous Single Detector Measurement of Multiple Fluorescent Sources," *Sensors Journal, IEEE*, vol. 13, pp. 1965-1971, 2013.

[21] A. Banerjee, Y. Shuai, R. Dixit, I. Papautsky, and D. Klotzkin, "Concentration dependence of fluorescence signal in a microfluidic fluorescence detector," *Journal of Luminescence*, vol. 130, pp. 1095-1100.

[22] J. Smith, "Disposable Point-of-Use Optical Biosensor for Multiple Biomarker Detection," presented at the BioCAS 2014, 2014.

[23] N. Ramachandran, J. V. Raphael, E. Hainsworth, G. Demirkan, M. G. Fuentes, A. Rolfs, et al., "Next-generation high-density self-assembling functional protein arrays," *Nat Meth*, vol. 5, pp. 535-538, 06//print 2008.

[24] B. O'Brien, Y. Lee, M. Marrs, J. Smith, M. Strnad, E. Forsythe, et al., "14.7" Active Matrix PHOLED Displays on Temporary Bonded PEN Substrates with Low Temperature IGZO TFTs," *SID Symposium Digest of Technical Papers*, vol. 70-2L, p. 447, 2013.

[25] J. Smith, M. Marrs, M. Strnad, R. Apte, J. Bert, D. Allee, et al., "Flexible Digital x-ray technology for far-forward remote diagnostic and conformal x-ray imaging applications," *Proc. SPIE* 8730, *Flexible Electronics*, 2013.

[26] J. T. K. Smith, B. A.; Kullman, D. E.; Obahiagbon, U.; Lee, Y.; O'Brien, B. P.; Raupp, G. B.; Anderson, K. S.; Blain Christen, J., "Application of Flexible OLED Display Technology to Point-of-Care Medical Diagnostic Testing," *Display Technology, Journal of*, vol. PP, p. 1, 2015.

[27] J. T. K. Smith, B. A.; Yong-Kyun Lee; O'Brien, B. P.; Bawolek, E. J.; Shah, S. S.; Christen, J. B., "Disposable point-of-use optical biosensor for multiple biomarker detection," *Biomedical Circuits and Systems Conference (BioCAS), 2014 IEEE*, pp. 268-271, 22-24 Oct. 2014 2014.

[28] S. Wagner and S. Bauer, "Materials for stretchable electronics," *Mrs Bulletin*, vol. 37, pp. 207-217, March 2012.

[29] A. Dominguez, G. Kunnen, M. Vetrano, J. Smith, M. Marrs, and D. R. Allee, "Development of a testbed for flexible a-Si:H photodiode sensing arrays," in *Proc. SPIE* 8730, *Flexible Electronics*, 87300H 2013, pp. 87300H-87300H-8.

[30] M. Marrs, E. Bawolek, J. T. Smith, G. B. Raupp, and D. Morton, "Flexible amorphous silicon PIN diode x-ray detectors," *Proc. SPIE* 8730, *Flexible Electronics*, 2013.

[31] J. T. Smith, B. O'Brien, L. Yong-Kyun, E. J. Bawolek, and J. B. Christen, "Application of Flexible OLED Display Technology for Electro-Optical Stimulation and/or Silencing of Neural Activity," *Display Technology, Journal of*, vol. 10, pp. 514-520, 2014.

[32] J. Cuzick, M. Arbyn, R. Sankaranarayanan, V. Tsu, G. Ronco, M. H. Mayrand, et al., "Overview of human papillomavirus-based and other novel options for cervical cancer screening in developed and developing countries," *Vaccine*, vol. 26 Suppl 10, pp. K29-41, Aug. 19, 2008.

[33] G. D'Souza, N. D. Gross, S. I. Pai, R. Haddad, K. S. Anderson, S. Rajan, et al., "Oral Human Papillomavirus (HPV) Infection in HPV-Positive Patients With Oropharyngeal Cancer and Their Partners," *J Clin Oncol*, Apr. 28, 2014.

[34] T. D. R. D. E. E. Panel, S. Banoo, D. Bell, P. Bossuyt, A. Herring, D. Mabey, et al., "Evaluation of diagnostic tests for infectious diseases: general principles," *Nat Rev Microbiol*, vol. 8, pp. S17-29, December 2010.

[35] G. F. Reed, F. Lynn, and B. D. Meade, "Use of coefficient of variation in assessing variability of quantitative assays," *Clin Diagn Lab Immunol*, vol. 9, pp. 1235-9, November 2002.

[36] J. Hu, S. Wang, L. Wang, F. Li, B. Pingguan-Murphy, T. J. Lu, et al., "Advances in paper-based point-of-care diagnostics," *Biosens Bioelectron*, vol. 54, pp. 585-97, Apr. 15 2014.

The present invention has been described in terms of one or more preferred embodiments, and it should be appreciated that many equivalents, alternatives, variations, and modifications, aside from those expressly stated, are possible and within the scope of the invention.

We claim:

1. A system for low-cost point-of-care immunoassay, comprising:
    a) an emitter comprising non-organic light emitting diodes (LEDs) or organic light emitting diodes (OLED) that emits light of a first color when pulsed with electrical current;
    b) a first optical interference filter that band-passes the light of the first color;
    c) a substrate comprising one or more protein biomarkers of interest to which biofluid from a patient is contacted, wherein, when the biofluid comprises an analyte that binds to protein biomarkers of interest, the analyte immobilizes fluorophores to the one or more protein biomarkers whereby the fluorophores and emit light of a second color when stimulated by the light of the first color;
    d) a second optical interference filter that band-passes the light of the second color;
    e) a photodiode detector that detects the light of the second color, wherein the detector is placed upon the second filter, the substrate, the first filter, and then the emitter;
    f) an op-amp charge integration circuit that converts current outputted from the photodiode detector into an output voltage; and
    g) a measuring unit that measures a ramp time of the output voltage, wherein the ramp time is used to determine a concentration of the fluorophores related to a concentration of the biomarkers.

2. The system as recited in claim 1, further comprising a 3D printed assembly configured to align a center of the substrate with the first filter and the second filter.

3. The system as recited in claim 1, wherein the substrate in c) is prepared by procedures comprising:
    i) depositing proteins onto the substrate;
    ii) incubating the proteins with the biofluid; and
    iii) incubating the proteins further with fluorophore-labeled detection antibodies associated with the protein biomarkers.

4. The system as recited in claim 3, wherein step ii) is repeated one or more times to achieve a desired sensitivity.

5. The system of claim 3, wherein the procedures further comprise a first step of silanizing the substrate.

6. The system as recited in claim 1, wherein the ramp time is a time interval that the output voltage takes to ramp from 0 volt to a supply voltage rail.

7. The system as recited in claim 1, wherein the ramp time is a time interval that the output voltage takes to ramp from a first voltage to a second voltage.

8. The system as recited in claim 1, wherein the first filter is deposited in the emitter.

9. The system as recited in claim 1, wherein the biofluid is serum.

10. The system as recited in claim 9, wherein the biomarkers are for papillomavirus.

11. The system as recited in claim 1, wherein the biomarkers are antibodies specific for HPV16 E7.

12. The system as recited in claim 1, wherein the substrate is a microscope slide.

13. The system of claim 1, wherein the op-amp charge integration circuit converts current to the output voltage using an op-charge integration time of at least 10 seconds.

14. The system of claim 1, wherein the op-amp charge integration circuit converts current to the output voltage using an op-charge integration time of about 30 seconds to about 60 seconds.

* * * * *